US010422741B2

(12) United States Patent
Sandsten et al.

(10) Patent No.: US 10,422,741 B2
(45) Date of Patent: Sep. 24, 2019

(54) WAVELENGTH BAND BASED PASSIVE INFRARED GAS IMAGING

(71) Applicant: FLIR Systems AB, Täby (SE)

(72) Inventors: Jonas Sandsten, Lomma (SE); Erik Ekerot, Solna (SE)

(73) Assignee: FLIR Systems AB, Täby (SE)

( * ) Notice: Subject to any disclaimer, the term of this patent is extended or adjusted under 35 U.S.C. 154(b) by 0 days.

(21) Appl. No.: 15/692,805

(22) Filed: Aug. 31, 2017

(65) Prior Publication Data
US 2018/0011009 A1 Jan. 11, 2018

Related U.S. Application Data

(63) Continuation of application No. PCT/EP2016/054449, filed on Mar. 2, 2016.
(Continued)

(51) Int. Cl.
*G01N 21/3504* (2014.01)
*G01N 21/31* (2006.01)
(Continued)

(52) U.S. Cl.
CPC ........ *G01N 21/3504* (2013.01); *G01J 3/0208* (2013.01); *G01J 3/2823* (2013.01);
(Continued)

(58) Field of Classification Search
CPC . G01N 21/3504; G01N 21/314; G01J 3/0208; G01J 3/2823; G01J 3/45; G01M 3/38
See application file for complete search history.

(56) References Cited

U.S. PATENT DOCUMENTS

| 5,306,913 A | 4/1994 | Noack et al. |
| 5,430,293 A * | 7/1995 | Sato ........................ G01M 3/38 250/330 |

(Continued)

FOREIGN PATENT DOCUMENTS

| GB | 2176889 | 1/1987 |
| WO | WO 03/044499 | 5/2003 |
| WO | WO-03044499 A2 * | 5/2003 .............. G01M 3/38 |

OTHER PUBLICATIONS

Alazarine et al.—WO 03/044499 A2—English Translation— Google Patents obtained May 3, 2019 (Year: 2019).*
(Continued)

*Primary Examiner* — David P Porta
*Assistant Examiner* — Jeremy S Valentiner
(74) *Attorney, Agent, or Firm* — Haynes and Boone, LLP

(57) ABSTRACT

Systems and methods disclosed herein, in accordance with one or more embodiments provide for imaging gas in a scene, the scene having a background and a possible occurrence of gas. In one embodiment, a method and a system adapted to perform the method includes: controlling a thermal imaging system to capture a gas IR image representing the temperature of a gas and a background IR image representing the temperature of a background based on a predetermined absorption spectrum of the gas, on an estimated gas temperature and on an estimated background temperature; and generating a gas-absorption-path-length image, representing the length of the path of radiation from the background through the gas, based on the gas image and the background IR image. The system and method may include generating a gas visualization image based on the gas-absorption-path-length image to display an output image visualizing a gas occurrence in the scene.

19 Claims, 17 Drawing Sheets

Related U.S. Application Data

(60) Provisional application No. 62/127,247, filed on Mar. 2, 2015.

(51) Int. Cl.
    *G01J 3/02*     (2006.01)
    *G01J 3/28*     (2006.01)
    *G01M 3/38*     (2006.01)
    *G01J 3/45*     (2006.01)
    *G01N 21/17*     (2006.01)

(52) U.S. Cl.
    CPC .................. *G01J 3/45* (2013.01); *G01M 3/38* (2013.01); *G01N 21/314* (2013.01); *G01N 2021/1793* (2013.01); *G01N 2021/3531* (2013.01)

(56) References Cited

U.S. PATENT DOCUMENTS

| | | | |
|---|---|---|---|
| 8,559,721 | B1 | 10/2013 | Bartholomew |
| 2003/0025081 | A1* | 2/2003 | Edner .................... G01M 3/38 250/339.09 |
| 2005/0134859 | A1* | 6/2005 | Kalayeh ................. G01N 21/31 356/437 |
| 2005/0156111 | A1 | 7/2005 | Racca et al. |
| 2006/0091310 | A1 | 5/2006 | Furry |
| 2008/0251724 | A1 | 10/2008 | Baliga et al. |
| 2008/0283753 | A1* | 11/2008 | Jensen ..................... G01J 3/36 250/339.02 |
| 2010/0008595 | A1 | 1/2010 | Riley et al. |
| 2010/0301214 | A1 | 12/2010 | Jonsson |
| 2013/0113939 | A1* | 5/2013 | Strandemar ............... G06T 5/10 348/164 |
| 2016/0238451 | A1 | 8/2016 | Zeng |

OTHER PUBLICATIONS

Messinger, David, "A method for quantification of gas plumes in thermal hyperspectral imagery", Algorithma NS Technologies for Multispectral, Hyperspectral, and Ultraspectral Imagery XI, 2005, pp. 218-228, Proceedings of SPIE vol. 5806, SPIE, Bellingham, WA.

Gross et al., "Remote Identification and Quantification of Industrial Smokestack Effluents via Imaging Fourier-Transform Spectroscopy", Environmental Science & Technology, Dec. 15, 2010, pp. 9390-9397, vol. 44, No. 24, American Chemical Society, Washington, D.C.

* cited by examiner

WAVELENGTH BAND BASED PASSIVE INFRARED GAS IMAGING

CROSS-REFERENCE TO RELATED APPLICATIONS

This application is a continuation of International Patent Application No. PCT/EP2016/054449 filed Mar. 2, 2016 and entitled "WAVELENGTH BAND BASED PASSIVE INFRARED GAS IMAGING," which is incorporated herein by reference in its entirety.

International Patent Application No. PCT/EP2016/054449 Filed Mar. 2, 2016 claims priority to and the benefit of U.S. Provisional Patent Application No. 62/127,247 filed Mar. 2, 2015 and entitled "WAVELENGTH BAND BASED PASSIVE INFRARED GAS IMAGING," which is hereby incorporated by reference in its entirety.

TECHNICAL FIELD

The present disclosure relates generally to imaging and visualizing gas and, in particular, to imaging and visualizing gas using infrared imaging systems and methods.

BACKGROUND

Thermal, or infrared (IR), images of scenes are often useful for monitoring, inspection and/or maintenance purposes, e.g. for monitoring gas leaks at an industrial plant. Typically, a thermal imaging device, e.g. in the form of a thermography arrangement or an infrared IR camera, is provided to capture infrared (IR) image data values, representing infrared radiation emitted from an observed scene. The captured IR image can after capturing be processed, displayed and/or saved, for example in the thermal imaging device or in a computing device connected to the thermal imaging device such as a tablet computer, a smartphone, a laptop or a desktop computer.

Thermal imaging devices, such as IR cameras, might be used for detecting gas occurrence, for example in the form of a gas cloud or gas plume e.g. from fugitive gas emissions or gas leaks, and for producing a visual representation of such gas occurrence as a gas infrared image. Such a gas infrared image can be used for visualizing gas occurrence or gas leaks, e.g. as smoke or a cloud on images presented on the viewfinder of a camera, on an integrated or separate display, or on an external computing device, thereby allowing the user to see gas occurrence in a scene observed and imaged by means of an IR camera. A variant of such techniques is called passive infrared gas imaging and is based on using radiation from a scene without any additional illumination for detecting gas.

However, a problem with conventional systems is that the sensitivity of the thermal imaging device might be too low to detect gas below a certain gas particle concentration or, in other words, the contrast between gas information and noise/interference in a generated gas infrared image is too low to identify gas. Another problem is that the sensitivity is further reduced by various physical aspects, such as varying temperatures and emissivity in the observed scene background, noise, other gases, aerosol particles and moving gas clouds.

In conventional technology, particularly using cooled thermal imaging devices, gas imaging may be based on the difference in absorption or transmission of infrared radiation in different wavelength bands. A problem, particularly with uncooled thermal imaging devices, is that when basing gas imaging on the difference in absorption or transmission of infrared radiation in selected wavelength bands, the bands cannot be made narrow due to high noise contribution by imaging device components such as filters, optical systems, wave guide and the detector itself. This means that physical characteristics of the system, such as noise or thermal interference might vary significantly with wavelength and will be more difficult to compensate for.

There is a need to address the problems of conventional systems to improve gas detection sensitivity in gas imaging with reduced complexity, size, weight, manufacturing cost and/or overall power consumption for imaging for example a wide range of gases without hardware reconfigurations that result in high cost and weight increase.

SUMMARY

Various techniques and embodiments of methods, systems and computer program products are disclosed for imaging gas in a scene having a background and a possible occurrence of gas. In various embodiments gas imaging is carried out by controlling a thermal imaging system to capture a gas IR image representing the temperature of a gas and a background IR image representing the temperature of a background based on a predetermined absorption spectrum of the gas, on an estimated gas temperature and on an estimated background temperature. A gas-absorption-path-length image, representing the length of the path of radiation from the background through the gas, is then generated based on the gas image and the background IR image.

In further variants, in accordance with one or more embodiments, the methods, systems and computer program products further comprise a selection of:

Generating a gas visualization image based on the gas-absorption-path-length image.

Controlling, for the capturing of the gas IR image, the thermal imaging system to capture radiation in a high absorption wavelength band A determined to include wavelengths with high absorption of radiation for the gas in the predetermined absorption spectrum; and/or controlling, for the capturing of the background IR image, the thermal imaging system to capture radiation in a low absorption wavelength band B determined to include wavelengths with low absorption of radiation for the gas in the predetermined absorption spectrum.

Determining the high absorption wavelength band A to include an absorption wavelength band G from the absorption spectrum of the gas; and/or determining the low absorption wavelength band B to at least partially overlap the high absorption wavelength band A.

Estimating the gas temperature $T_G$ based on a measured ambient air temperature retrieved from an ambient air temperature sensor; and/or estimating the gas temperature $T_G$ based on a previously captured gas IR image.

Estimating the background temperature $T_B$ based on a previously captured background IR image.

Generating a gas-absorption-path-length image further based on a gas to background difference relation.

Determining the high absorption wavelength band A further comprising:

determining an absorption wavelength band G based on the absorption spectrum of the gas, wherein the absorption wavelength band G is determined to include at least a local minimum of the absorption spectrum; and determining the high absorption wavelength band A as including the absorption wavelength band G and possibly a predetermined wavelength margin.

The predetermined wavelength margin being a selection of:

a first wavelength margin G_MARGIN1 applied to the lower endpoint of the absorption wavelength band G; and/or a second wavelength margin G_MARGIN2 applied to the higher endpoint of the absorption wavelength band G.

Determining the low absorption wavelength band B further comprising:

determining the low absorption wavelength band B as having a width greater than the high absorption wavelength band A, possibly within a predetermined wavelength margin.

The predetermined wavelength margin being a selection of:

a first wavelength margin A_MARGIN1 below the lower endpoint of high absorption wavelength band A; and/or a second wavelength margin A_MARGIN2 above the higher endpoint of high absorption wavelength band A.

Determining the low absorption wavelength band B further comprising:

obtaining an objective function indicative of contrast and dependent on pixel values of the gas-absorption-path-length image;

generating an optimized wavelength band B by evaluating the objective function on wavelength band B shifted within a band constraint and by selecting a shifted wavelength band B with an evaluated objective function value representing a local minimum as the optimized wavelength band B.

Determining the low absorption wavelength band B comprising the excluding of the absorption wavelength band G from the low absorption wavelength band B.

Generating a visual presentation image based on pixel values of the gas-absorption-path-length image and a palette, wherein said palette comprises grayscales and/or colors associated to mutually exclusive ranges of pixel values.

Determining a water wavelength band C to improve contrast in a generated gas-absorption-path-length image based on a predetermined water absorption spectrum, wherein the water wavelength band C includes at least a local minimum of the water absorption spectrum and preferably excludes the high absorption wavelength band A and/or the low absorption wavelength band B;

controlling, for capturing a water image, the thermal imaging system to capture radiation within the water wavelength band C;

generating the gas-absorption-path-length image further based on the water image.

A thermal imaging device for imaging gas comprising a thermal imaging system and a processor, being adapted to perform any of the steps and functions of the embodiments described herein.

A computer-readable medium for imaging gas, comprising stored thereon: non-transitory information for performing any of the embodiments described herein; and/or non-transitory information configured to control a processor/processing unit to perform any of the steps or functions described herein.

A computer program product for imaging gas, comprising code portions adapted to control a processor to perform any of the steps or functions of any of embodiments described herein.

The scope of the invention is defined by the claims, which are incorporated into this section by reference. A more complete understanding of embodiments of the invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

Embodiments of the present disclosure and their advantages are best understood by referring to the detailed description that follows. It should be appreciated that like reference numerals are used to identify like elements illustrated in one or more of the figures.

DETAILED DESCRIPTION

Introduction

The disclosure relates to imaging and visualizing gas or fugitive gas using infrared IR sensors or detectors and image processing. An example of a use case is the inspection with a thermal imaging device of a part of an industrial complex handling gas.

Figure 1:
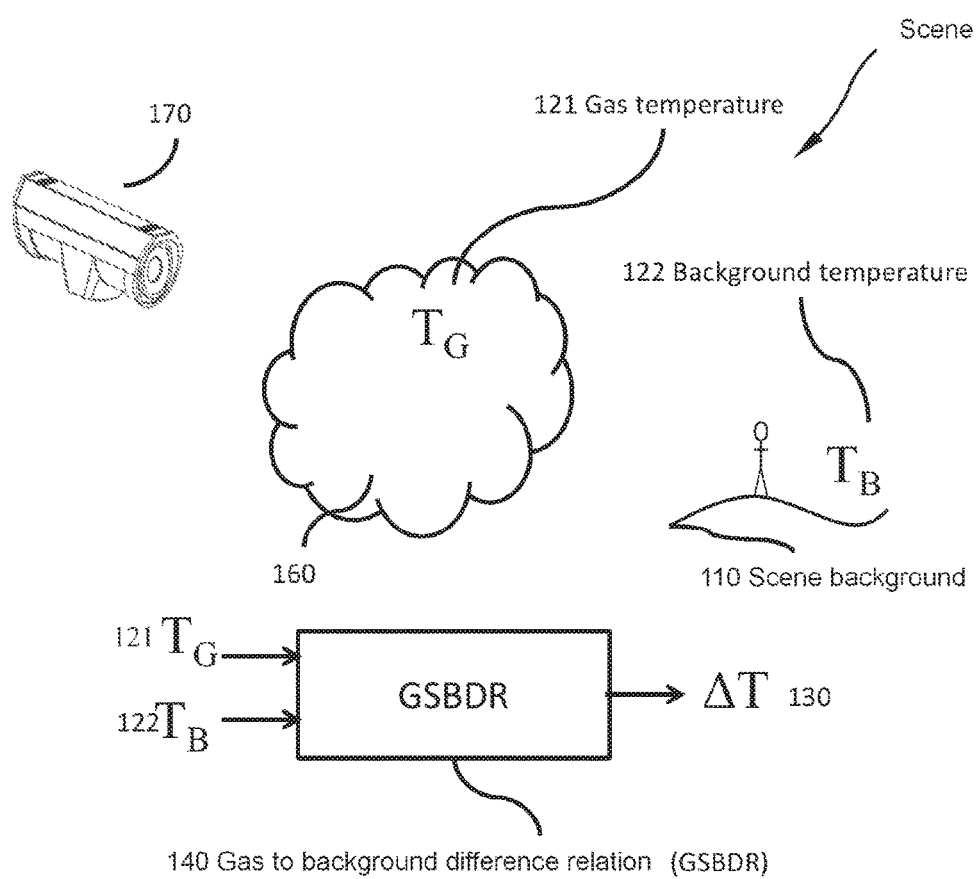
FIG. 1 shows a schematic view of passive imaging of gas based on a background temperature difference $\Delta T$, in accordance with of one or more embodiments of the disclosure.

In particular the disclosure relates to passive gas imaging that uses thermal background radiation within the infrared region and can be used to image gas for example against a cold background, in this case imaging thermal emission or radiation from the gas, or used against a warm background, in that case imaging absorption by the gas of thermal radiation from the background. Imaging of gas is based on the difference in gas temperature $T_G$ and background temperature $T_B$, hereinafter referred to as gas to background temperature difference $\Delta T$. However, the sensitivity of a thermal imaging system is dependent on the difference in gas temperature $T_G$ and background temperature $T_B$, FIG. 1 shows a schematic view of a method and an apparatus for passive imaging of gas based on background temperature difference $\Delta T$ 130, in accordance with one or more embodiments. A thermal imaging device 170 is adapted to capture radiation within controllable wavelength bands and thus to produce infrared images, herein also called IR images or thermal images, representing a particular selected wavelength band of infrared radiation from a scene. Between the thermal imaging device 170 (also referred to as a thermal imaging system) and a scene background 110 there is gas 160 present in the form of aerosol particles or gas molecules, in the figures illustrated as a gas occurrence in the shape of a gas cloud. The scene background 110 has a background temperature TB 122, and the gas has a gas temperature TG 121. A temperature difference parameter preferably in the form of a gas to background temperature difference $\Delta T$ 130 can be determined or calculated based on the background temperature TB 122 and the gas temperature TG 121 by a gas to background difference relation 140. In a accordance with one or more embodiments, a thermal imaging device 170 is configured and/or controlled to capture and/or generate a selection of inter alia a background IR image representing the thermal radiation from the background in a scene, a gas IR image representing a gas occurrence between the thermal imaging device and a background in a scene and/or a possible other IR image representing other phenomena in the scene.

In one or more embodiments, a gas-absorption-path-length image representing the length of the path of radiation from the scene background 110 through a gas occurrence in the scene can be generated based on a gas image, a background image and optionally the temperature difference parameter $\Delta T$ 130. In yet an embodiment, gas is visualized in a gas visualization image presentable or presented to the user on a display, this image being based on pixel values of the gas-absorption-path-length image. In yet an embodiment a background temperature $T_B$ 122 derived from a pixel value in a background image and a gas temperature $T_G$ 121 derived from a pixel value in a gas image are used to determine the temperature difference parameter $\Delta T$ 130.

In one or more embodiments, the gas temperature $T_G$ is estimated based on a measured ambient air temperature retrieved from an ambient air temperature sensor and/or based on a previously captured gas IR image that comprises a representation of the intensity of infrared radiation within a first wavelength band A substantially including wavelengths of infrared radiation with high absorptance values for the gas in an absorption spectrum and/or low transmittance values in a transmission spectrum. In other words, the first wavelength band A is a high absorption wavelength band that includes wavelengths significantly affected by the presence of the gas to be imaged. In a case where the gas has a temperature higher than the ambient air temperature or the background temperature there is radiation from the gas in an emission spectrum. The first wavelength band A is herein also called high absorption wavelength band A.

In one or more embodiments, the background temperature $T_B$ is estimated based on a previously captured background IR image that comprises a representation of the intensity of infrared radiation within a second wavelength band B substantially including wavelengths of infrared radiation with low absorptance values for the gas in an absorption spectrum and/or high transmittance values in a transmission spectrum. In other words, the second wavelength band B is a low absorption wavelength band and/or a high transmission wavelength band that includes wavelengths insignificantly affected by the presence of the gas to be detected. The second wavelength band B is herein also called low absorption wavelength band B.

Figure 2A:
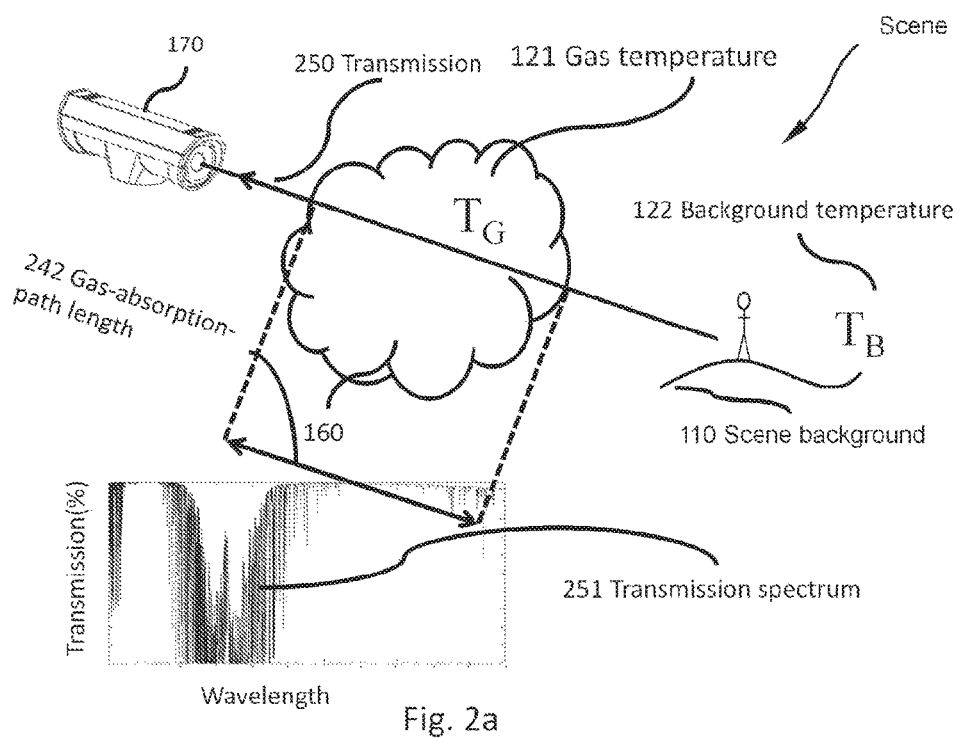
FIG. 2a illustrates a method for imaging gas, in accordance with one or more embodiments of the disclosure.

FIG. 2a illustrates a method for imaging gas in accordance with one or more embodiments for example applicable in a situation where the background temperature TB 122 is higher than the gas temperature TG 121, i.e. the scene background is warmer than the gas 160. A fraction of the energy or infrared radiation emitted from the scene background 110 is transmitted through the gas 160, indicated as radiation transmission 250 with a gas-absorption-path length 242, to the detector in a thermal imaging device 170. In one or more embodiments this fraction can be determined by using a predetermined relation for example based on a transmission spectrum 251.

Figure 2B:
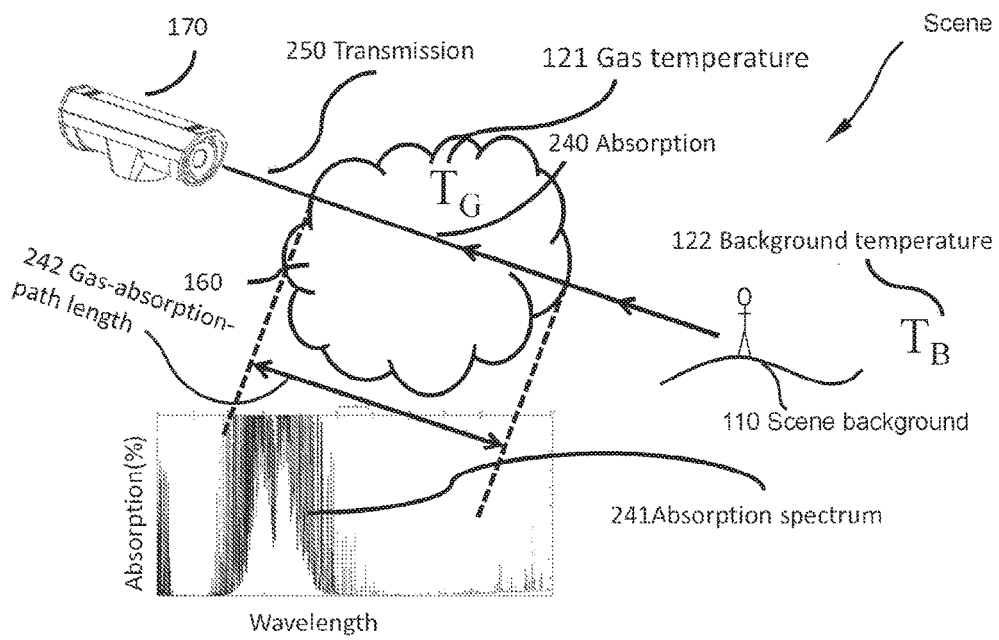
FIG. 2b illustrates a further method for imaging gas, in accordance with one or more embodiments of the disclosure.

FIG. 2b illustrates a method for imaging gas in accordance with one or more embodiments for example applicable in a situation where the background temperature TB 122 is lower than the gas temperature TG 121, i.e. the scene background is colder than the gas. A fraction of the energy or infrared radiation emitted from the scene background 110 is transmitted through the gas, indicated as radiation transmission 250 with a gas-absorption-path-length 242, to the detector in a thermal imaging device 170. In one or more embodiments this transmitted fraction can be determined by using a predetermined relation for example based on an absorption spectrum 241.

By controlling the thermal imaging system to capture radiation in a high absorption wavelength band A including wavelengths significantly affected by the presence of the gas to be detected, and to capture radiation in a low absorption wavelength band B including wavelengths insignificantly affected by the presence of the gas to be detected, a background IR image and a gas IR image are generated. Based on the background IR image, on the gas IR image and dependent on a transmission spectrum 251 and/or on an absorption spectrum 241, a gas-absorption-path-length image with improved contrast is generated in a system with improved sensitivity and/or improved signal to noise ration.

Figure 3:
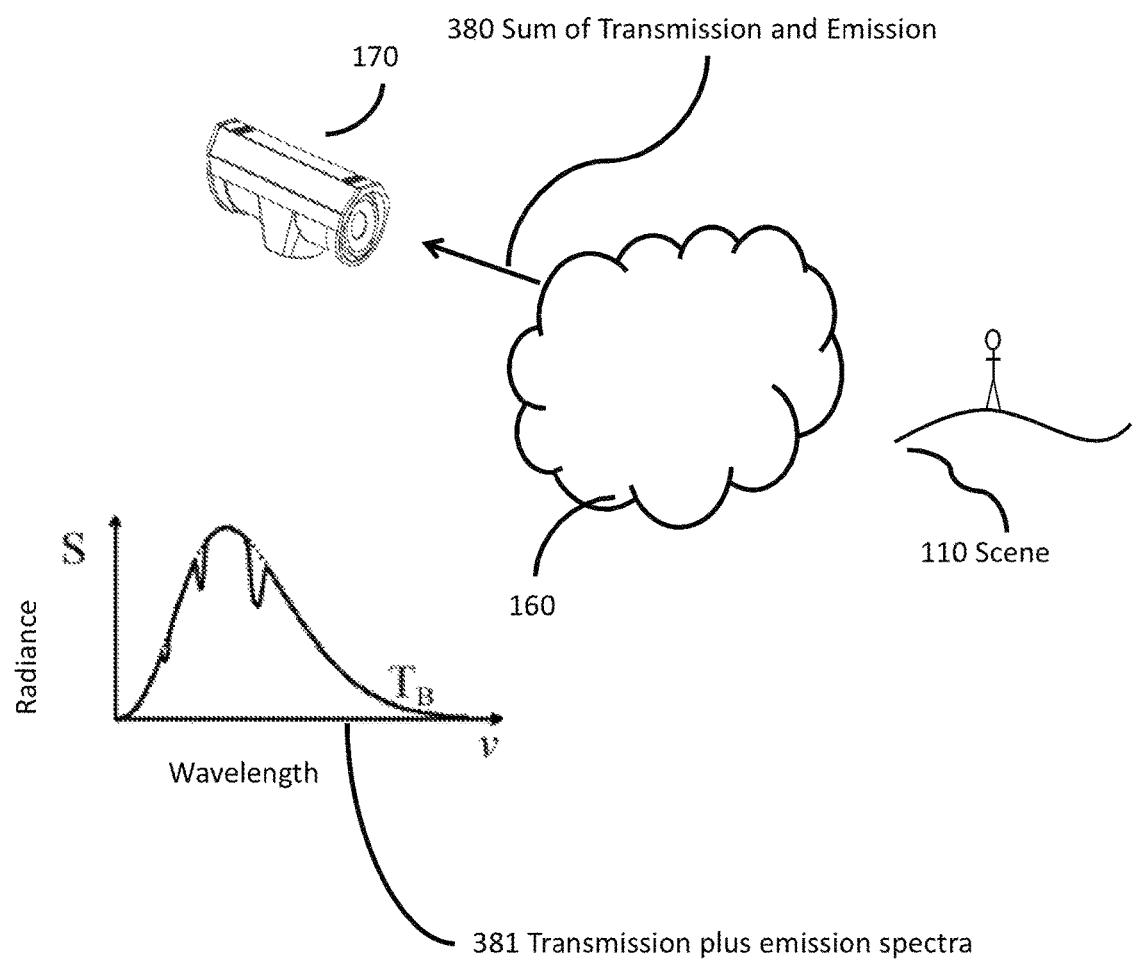
FIG. 3 illustrates a method for imaging gas in a case when the background temperature $T_B$ is lower than the gas temperature $T_G$, in accordance with one or more embodiments of the disclosure.

FIG. 3 illustrates one or more embodiments applied in a situation where the background temperature $T_B$ is lower than the gas temperature $T_G$, i.e. the background is colder than the gas 160. The thermal imaging system 170 is controlled to capture radiation in a low absorption wavelength band B including wavelengths less affected or not so affected, i.e. insignificantly affected by the presence of the gas to be detected, and to capture radiation in a high absorption wavelength band A including wavelengths more affected, i.e. significantly affected by the presence of the gas to be detected. There is also radiation emitted from the gas 160 in wavelengths in an emission spectrum. The thermal imaging system is controlled to capture radiation comprising a sum 380 of transmission through the gas and emission from the gas 160. A gas-absorption-path-length image is generated based on a transmission plus emission spectrum 381 being a sum of a transmission spectrum and an emission spectrum.

Figure 4:
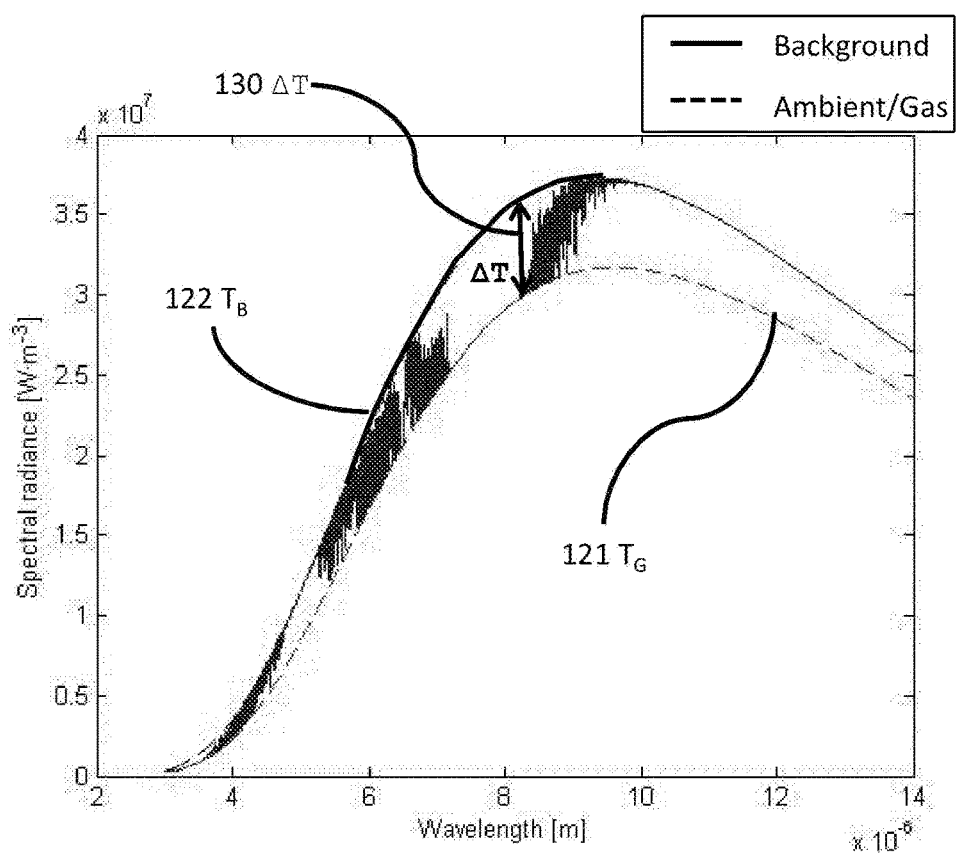
FIG. 4 illustrates in a graph an example on how gas temperature $T_G$, background temperature $T_B$ and gas to background temperature difference $\Delta T$ varies with the wavelength of the infrared radiation from a scene having a gas occurrence.

FIG. 4 is a graph showing radiance from a scene in relation to wavelength in the infrared range, the scene comprising a background and a gas occurrence in the ambient atmosphere in the scene. Translated to temperature corresponding to the radiance related to wavelength, this graph shows an example on how the gas temperature $T_G$ indicated with an intermittently drawn line, the background temperature $T_B$ indicated with a fully drawn line and the gas to background temperature difference $\Delta T$ 130, i.e. the difference $T_B-T_G$, varies with the wavelength of the infrared radiation from the scene.

Figure 5:
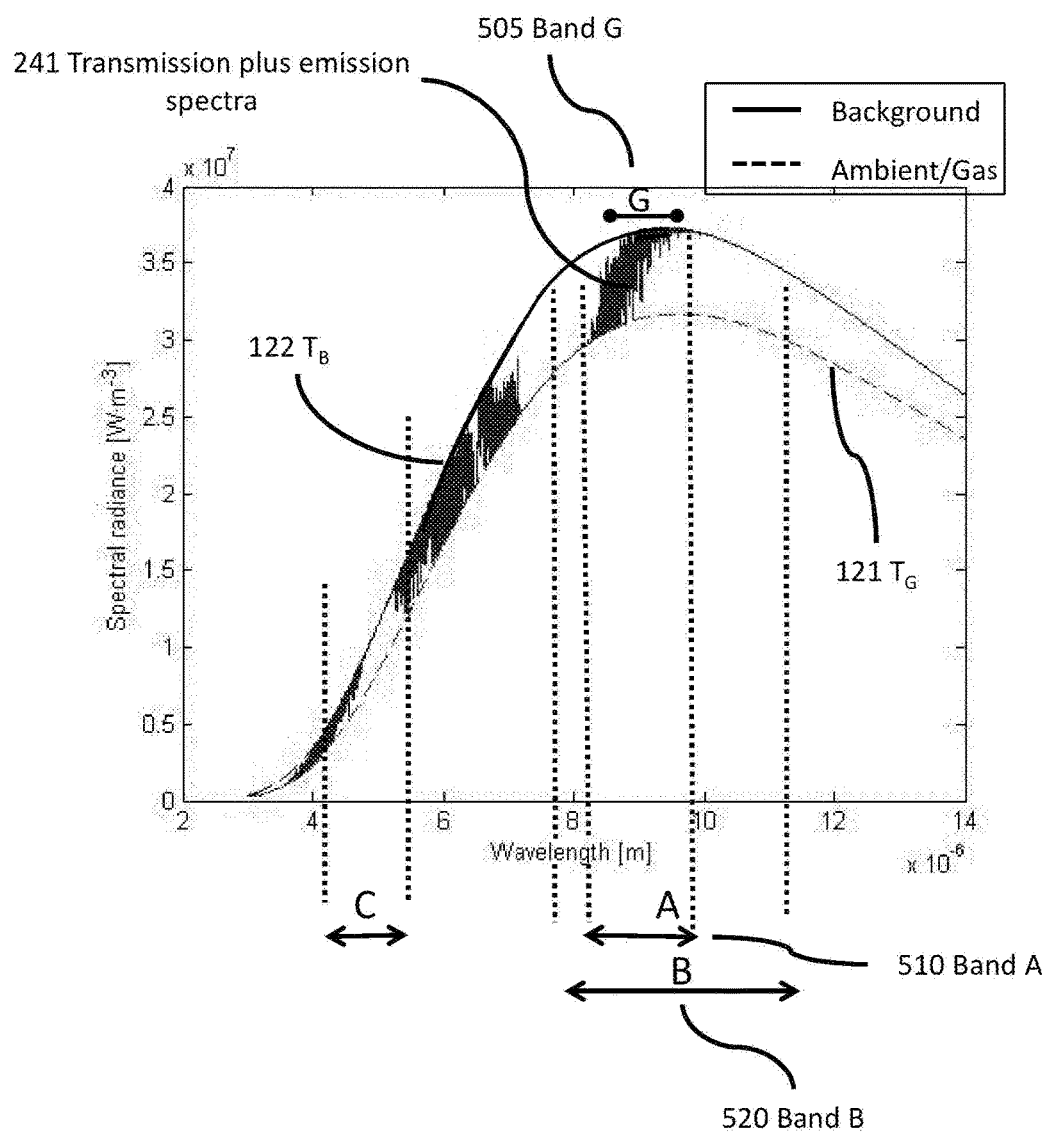
FIG. 5 illustrates in a graph an example of a wavelength band A 510 and a wavelength band B 520 determined to improve contrast in a generated gas-absorption-path-length image, in accordance with one or more embodiments of the disclosure.

FIG. 5 illustrates by means of a temperature/wavelength relation similar to that of FIG. 4 an example of one or more embodiments wherein a high absorption wavelength band A 510 and a low absorption wavelength band B 520 have been determined for the purpose to improve contrast in a generated gas-absorption-path-length image based on a predetermined absorption spectrum 241 of the gas, an estimated gas temperature $T_G$ 121 and an estimated background temperature $T_B$ 122. Wavelength band B 520 is selected to include wavelengths less affected or not so affected, i.e. insignificantly affected by the presence of the gas to be detected. Wavelength band A 510 is selected to include wavelengths more or strongly affected, i.e. significantly selected by the presence of the gas to be detected. In one or more embodiments, wavelength band A 510 includes an absorption wavelength band G 505 from the absorption spectrum 241 (FIG. 2*b*), i.e. a subset of the absorption spectrum significantly affected by the presence of the gas to be imaged, or expressed in a different aspect as a subset of a transmission spectrum less affected by the presence of the gas to be imaged. Furthermore, the low absorption wavelength band B 520 at least partially overlaps wavelength band A 510, thereby minimizing variations between wavelength band A 510 and wavelength band B 520 in emission/emissivity represented by values in the emission spectrum. Thereby an improved sensitivity and an improved signal to noise ratio is achieved in the thermal imaging system resulting in improved contrast in a generated gas-absorption-path-length image. Another effect by one or more embodiments is an elimination or simplification of the complexity of compensating for varying emission/emissivity in a scene.

System Embodiments

Figure 6:
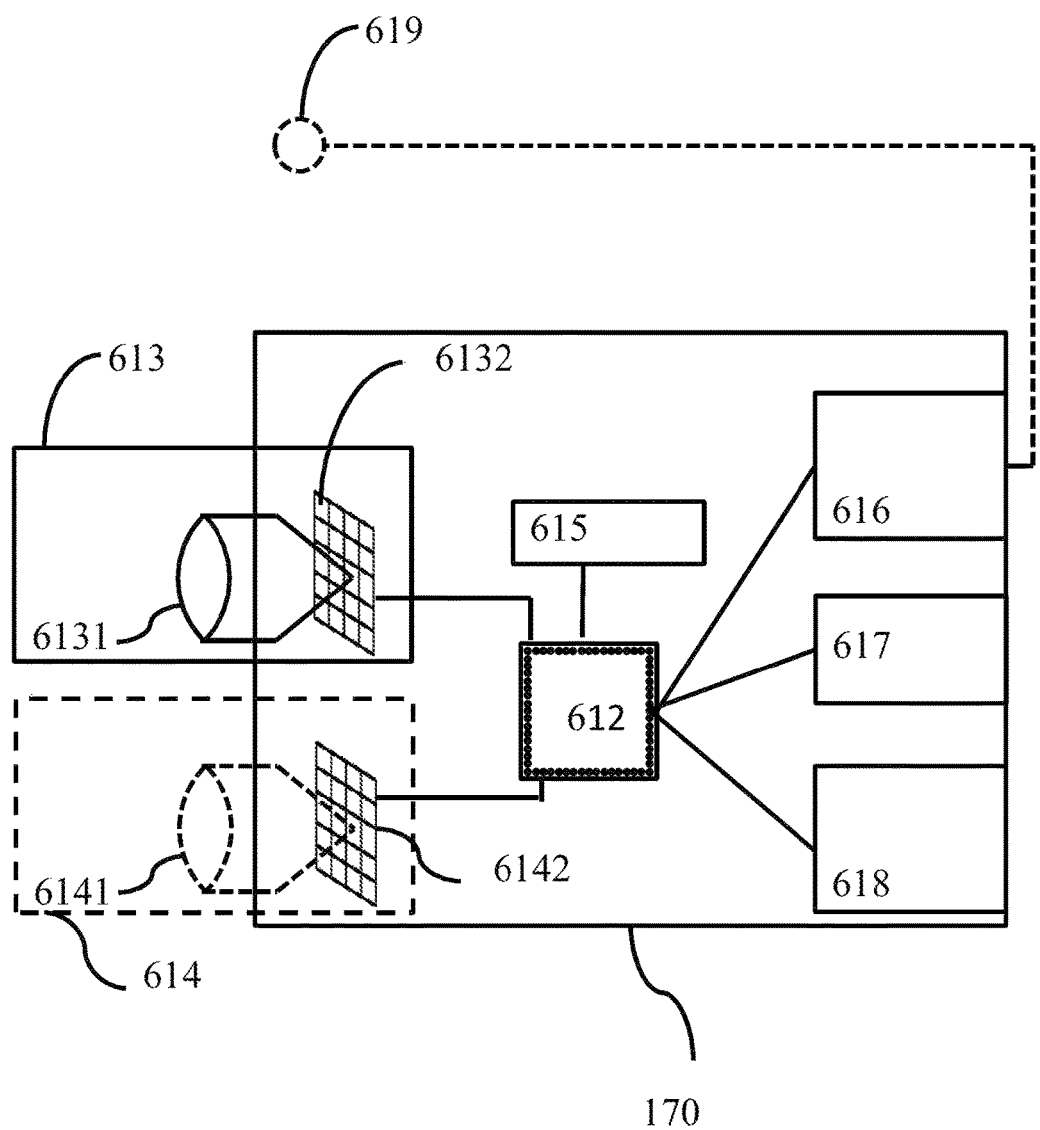
FIG. 6 shows a schematic view of a thermal imaging device, in accordance with one or more embodiments of the disclosure.

FIG. 6 shows a schematic view of one or more embodiments of a thermal imaging device or system 170, e.g. in the form of a thermography arrangement or an infrared IR camera. The thermal imaging device 170 comprises a first infrared (IR) imaging system 613 that is configured and/or controllable to capture infrared (IR) images in the form of IR image data values/pixel values, representing infrared radiation emitted from an observed scene within one or more selectable wavelength bands A, B or C. The infrared (IR) imaging system 613 is further communicatively coupled to a processor 612.

The first infrared (IR) imaging system 613 is further configured to receive control data and to trigger the capturing of an IR image of a scene within a selected wavelength band in response to said control data. The first infrared (IR) imaging system 613 is further arranged to send a signal frame or data frame of IR image data values representing a captured image to the processor 612. IR image data typically include data values for example represented in an instance of a data structure, such as an image data frame as mentioned. The processor/processing unit 612 is provided with specifically designed programming or program code portions adapted to control the processing unit to perform the steps and functions of one or more embodiments of the method and/or methods described herein.

The thermal imaging device 170 further comprises at least one memory 615 configured to store data values or parameters received from a processor 612 or to retrieve and send data values or parameters to a processor 612. A communications interface 616 is configured to send or receive data values or parameters to or from a processor 612 to or from external or internal units or sensors via the communications interface 616. An optional input device 617 is configured to receive an input or an indication from a user, e.g. an input of a user indicating a command to execute the imaging of a gas-absorption-path-length image.

In one or more embodiments, the thermal imaging device 170 further comprises a display 618 configured to receive a signal from a processor 612 and to display the received signal as a displayed image, e.g. to display a visual representation of a gas-absorption-path-length image to a user of the thermal imaging device 170. In one or more embodiments, the display 618 is integrated with a user input device 617 configured to receive a signal from a processor 612 and to display the received signal as a displayed image and receive input or indications from a user, e.g. by comprising touch screen functionality and to send a user input signal to said processor/processing unit 612.

In one or more embodiments, the thermal imaging device 170 further comprises an ambient air temperature sensor 619 configured to measure ambient air temperature and generate an ambient air temperature data value and provide the ambient air temperature data value to the processor 612 receiving, polling or retrieving the ambient air temperature data value. In one or more embodiments, the ambient air temperature sensor 619 is communicatively coupled to the processor 612 directly or via the communications interface 616, and may be provided as an external or an internal unit.

In one or more embodiments, the thermal imaging device 170 further optionally comprises a second infrared (IR) imaging system 614, preferably with properties and functions similar to those of the first infrared (IR) imaging system 612 described above. The second infrared (IR) imaging system 614 is similarly configured and/or controllable to capture infrared (IR) images in the form of IR image data values/pixel values, representing infrared radiation emitted from an observed scene within one or more selectable wavelength bands A, B or C. The second infrared (IR) imaging system 614 is further communicatively coupled to a processor 612, and is further configured to receive control data and to trigger the capturing of an IR image of a scene within a selected wavelength band in response to said control data. The second infrared (IR) imaging system 614 is further arranged to send a signal frame of IR image data values representing an infrared (IR) image to the processor 612.

Typically, the described infrared (IR) imaging systems 613, 614 each comprises an infrared (IR) optical system 6131, 6141, e.g. comprising a lens, possible zoom functionality and focus functionality 6131, together with a corresponding infrared (IR) sensor 6132, 6142, for example comprising a micro-bolometer focal plane array.

Examples of Controllable/Selectable Wavelength Bands

The described infrared (IR) imaging systems 613, 614 are configured and/or controllable to capture infrared (IR) images in the form of IR image data values/pixel values, representing infrared radiation emitted from an observed scene within a preferably continuous subset of a plurality of wavelength bands A, B or C. One or more of the wavelength bands may be at least partly overlapping.

In one example, wavelength band A is selected as 7-9 μm and wavelength band B is selected as 9-15 μm, where the first infrared (IR) imaging system 613 is configured to capture gas IR images in the form of IR image data values/pixel values, representing infrared radiation emitted from an observed scene within 7-8.6 μm, and where the second infrared (IR) imaging system 614 is configured to capture background IR images in the form of IR image data values/pixel values, representing infrared radiation emitted from an observed scene within 9-12 μm.

Further Examples of Wavelength Bands

Table 1 shows examples of ranges of wavelength bands for different gases that may be used in embodiments described herein. So for example and as shown in the table, embodiments of a method or a device as described herein may be devised for operating on CO2 and would in this example have a high absorption wavelength band A in the range of 4.2 μm-4.6 μm and a low absorption filter B in the range of 4.4 μm-4.6 μm.

TABLE 1

Examples of wavelength bands for different gases

| Gas | High absorption Wavelength band A | Low absorption Wavelength band B |
|---|---|---|
| Methane 1 | 3.2 μm-3.6 μm | 3.4 μm-3.6 μm |
| Methane 2 | 7.0 μm-9.0 μm | 8.5 μm-9.0 μm |
| CO2 | 4.2 μm-4.6 μm | 4.4 μm-4.6 μm |
| CO + N20 | 4.52 μm-4.87 μm | 4.67 μm-4.87 μm |
| Refrigerants | 8.0 μm-9.0 μm | 8.6 μm-9.0 μm |
| SF6 | 10.3 μm-11.1 μm | 10.7 μm-11.1 μm |

Spatial Sensor Configuration

Figure 7A:
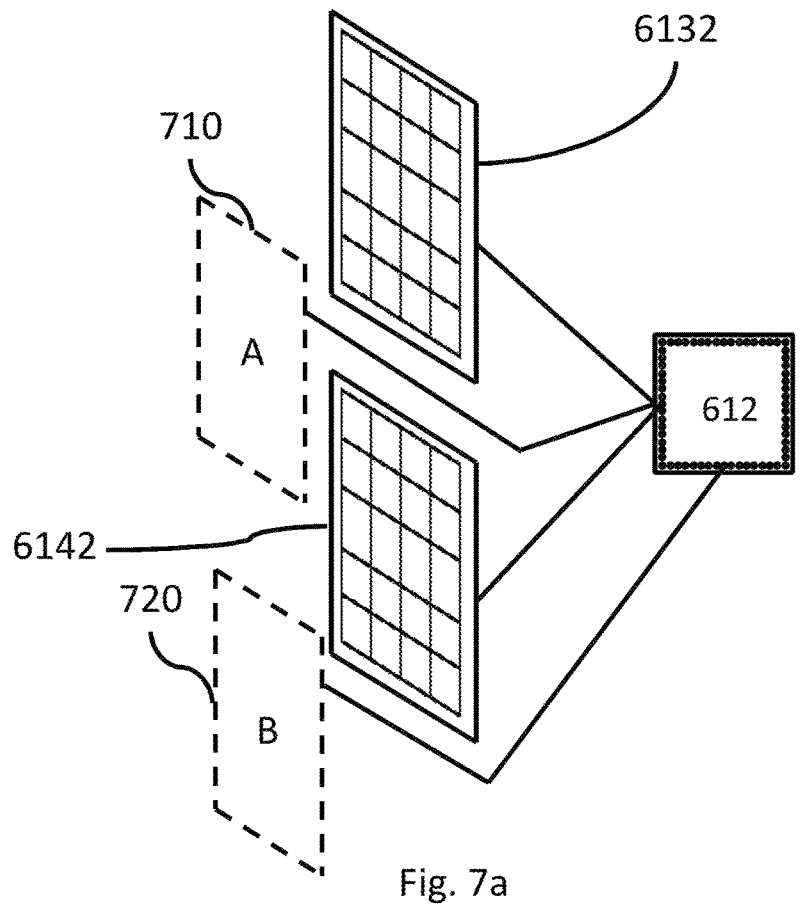
FIG. 7a shows a schematic view of a spatial sensor configuration in a thermal imaging device, in accordance with one or more embodiments of the disclosure.

FIG. 7a shows a schematic view of infrared sensors 6132, 6142 in a thermal imaging device 170 (cf. FIG. 6) configured to capture a gas IR image and a background IR image according to one or more embodiments.

This can also be referred to as a spatial sensor configuration. A first infrared (IR) imaging system 613 (cf. FIG. 6), comprised in the thermal imaging device 170, comprises an image sensor 6132 configured to capture a gas IR image. The sensor 6132 is configured to capture infrared radiation within a high absorption wavelength band A. The first infrared (IR) imaging system 613 optionally comprises an optical gas filter 710 in the optical path of the sensor 6132 configured with a passband of infrared radiation within said high absorption wavelength band A. A second infrared (IR) imaging system 614 (cf. FIG. 6), comprised in the thermal imaging device 170, comprises an image sensor 6142 configured to capture a background IR image. The sensor 6142 is configured to capture infrared radiation within a low absorption wavelength band B. The second infrared (IR) imaging system 614 optionally comprises a background optical filter 720 in the optical path of the sensor 6142 configured with a passband of infrared radiation within said low absorption wavelength band B.

The sensor 6132, comprised in the first infrared (IR) imaging system 613, is configured to capture a gas IR image simultaneously, substantially simultaneously, or with a time interval, with the sensor 6142, comprised in the second infrared (IR) imaging system 613, capturing a background IR image.

In one or more embodiments, the processor 612 is adapted to send control data to the first infrared (IR) imaging system to trigger the sensor 6132 to capture infrared radiation within the high absorption wavelength band A, and/or is adapted to send control data the second infrared (IR) imaging system to trigger the sensor 6142 to capture radiation within the low absorption wavelength band B.

In one or more embodiments comprising one or more optical filters, the processor 612 is adapted to send control data to the first infrared (IR) imaging system to configure the gas optical filter 710 with a pass band equal to wavelength band A and adapted to send control data to the second infrared (IR) imaging system to configure the background optical filter 720 with a pass band equal to wavelength band B. A combination of controllable sensor and controllable optical filter are provided in one or more embodiments.

Temporal Sensor Configuration

Figure 7B:
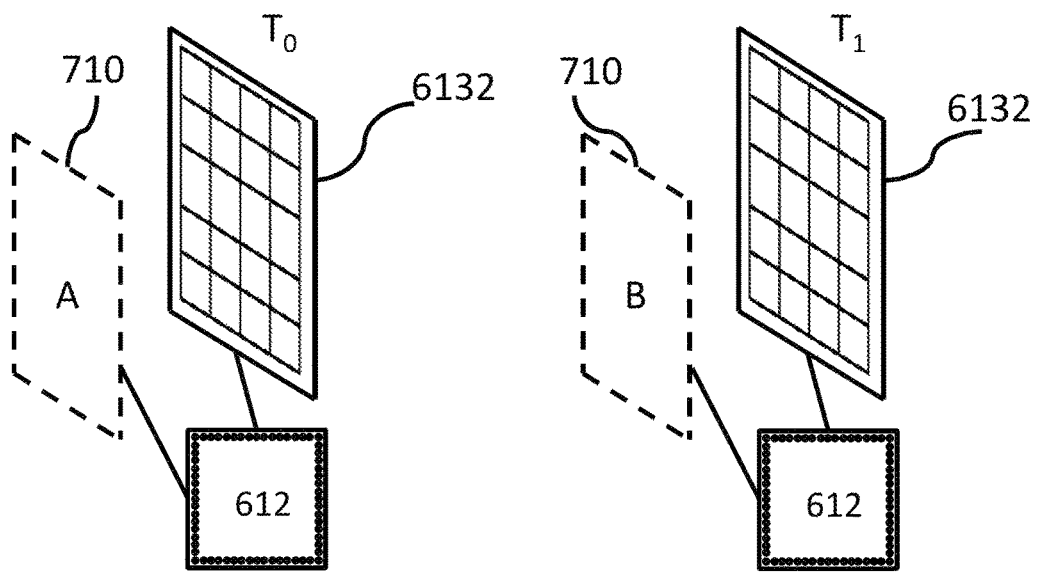
FIG. 7b shows a schematic view of a temporal sensor configuration in a thermal imaging device, in accordance with one or more embodiments of the disclosure.

FIG. 7b shows a schematic view of an infrared sensor 6132, 6142 in a thermal imaging device 170 (cf. FIG. 6) configured to capture a gas IR image and a background IR image according to one or more embodiments. This can also be referred to as a temporal sensor configuration. A first infrared (IR) imaging system 613, comprised in the thermal imaging device 170, comprises an image sensor 6132 configured to capture a gas IR image at time $T_0$ and a background IR image at time $T_1$. In one or more embodiments, the sensor 6132 is at time $T_0$ configured to capture infrared radiation within a high absorption wavelength band A. The first infrared (IR) imaging system 613 optionally comprises an optical filter 710 in the optical path of the sensor 6132 configured at time $T_0$ with a passband of infrared radiation equal to a high absorption wavelength band A and configured at time $T_1$ with a passband of infrared radiation equal to a low absorption wavelength band B.

In one or more embodiments, the processor 612 is adapted to send control data to the first infrared (IR) imaging system to configure the captured wavelength band of the sensor 6132 to the high absorption wavelength band A and to trigger the capturing of a gas IR image at time $T_0$, and to configure the captured wavelength band of the sensor 6132 to the low absorption wavelength band B and to trigger the capturing of a gas IR image at time $T_1$. Typically, there is a short time lapse between the time $T_0$ and the time $T_1$, suitably selected to reconfigure the sensor for different wavelength bands.

In one or more embodiments comprising one or more optical filters, the processor 612 is adapted to send control data to the first infrared (IR) imaging system to configure the optical filter 710 with a pass band equal to the high absorption wavelength band A at time $T_0$ and to configure the optical filter 710 with a pass band equal to the low absorption wavelength band B at time $T_1$. A combination of controllable sensor and controllable optical filter are provided in one or more embodiments also in a temporal sensor configuration.

Intertwined Sensor Configuration

Figure 8A:
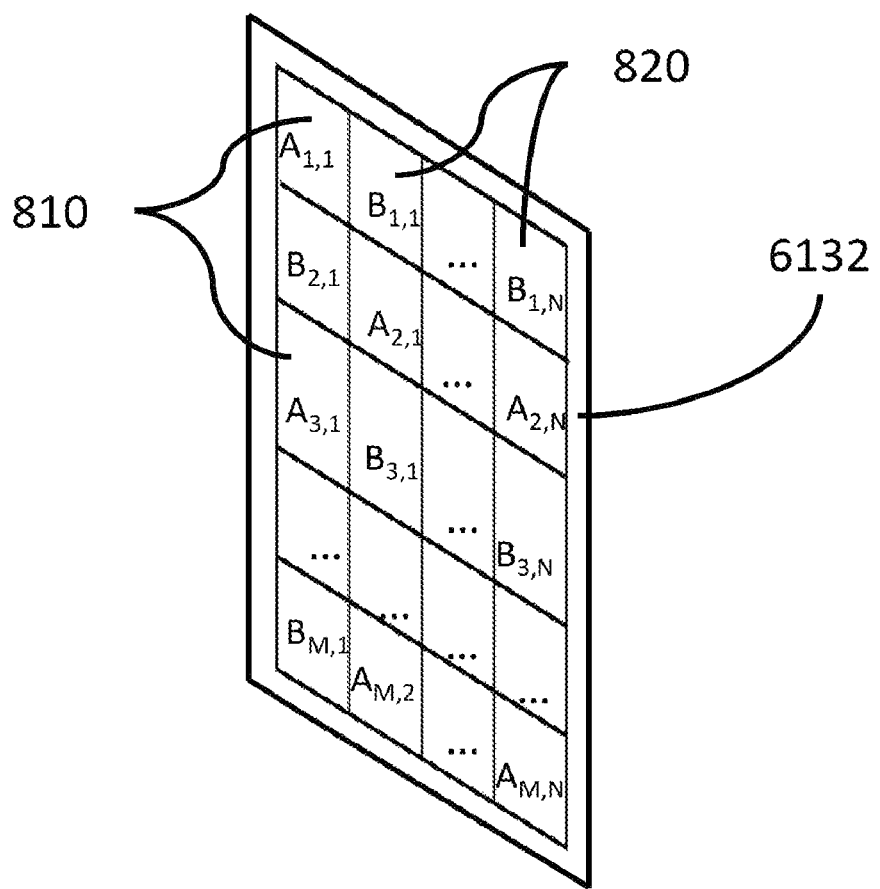
FIG. 8a shows a schematic view of an intertwined sensor configuration in a thermal imaging device, in accordance with one or more embodiments of the disclosure.

FIG. 8a shows a schematic view of an infrared sensor 6132 in a thermal imaging device configured to capture a gas IR image and a background IR image according to one or more embodiments. This can also be referred to as an intertwined sensor configuration and has the additional advantage of eliminating the need for aligning or registering the gas image and the background image.

A first infrared (IR) imaging system 613, comprised in the thermal imaging device 170 (cf. FIG. 6), comprises an image sensor 6132 configured with a first set of detector elements for capturing gas related radiation, here called a gas set of detector elements 810, and with a second set of detector elements for capturing background related radiation, here called a background set of detector elements 820. The first and the second sets of detector elements are intertwined such that detector elements 810 capturing infrared radiation within a high absorption wavelength band A alternate with detector elements 820 capturing infrared radiation within a low absorption wavelength band B in both rows and columns of the sensor 6132.

The processor 612 is adapted to send control data to configure the gas set detector elements 810 to capture infrared radiation within the high absorption wavelength band A, and to configure background set detector elements 820 to capture infrared radiation within wavelength band B. The processor 612 is further adapted to send control data to the first infrared (IR) imaging system to trigger the capturing of a gas IR image by the gas set detector elements 810 and to trigger the capturing of a background IR image by the background set detector elements 820.

Interlaced Sensor Configuration

Figure 8B:
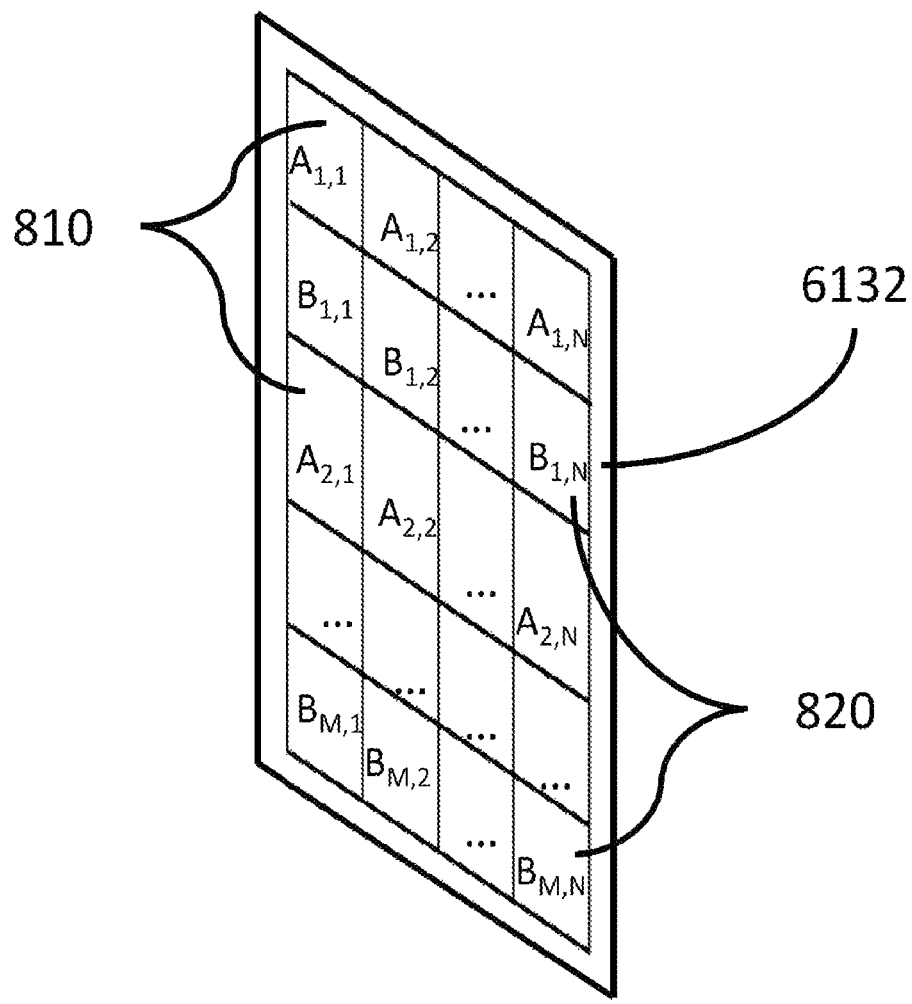
FIG. 8b shows a schematic view of an interlaced sensor configuration in a thermal imaging device, in accordance with one or more embodiments of the disclosure.

FIG. 8b shows a schematic view of an infrared sensor 6132 in a thermal imaging device configured to capture a gas IR image and a background IR image according to one or more embodiments. This can also be referred to as an interlaced sensor configuration and has the additional advantage of eliminating the need for aligning or registering the gas image and the background image.

A first infrared (IR) imaging system, comprised in the thermal imaging device 170 (cf. FIG. 6), comprises an image sensor 6132 configured with a first set of detector elements for capturing gas related radiation, here called a gas set of detector elements 810, and with a second set of detector elements for capturing background related radiation, here called a background set of detector elements 820. The rows of detector elements are interlaced such that gas set detector elements 810 capturing infrared radiation within a high absorption wavelength band A alternate with background set detector elements 820 capturing infrared radiation within a low absorption wavelength band B in rows of the sensor 6132. For example, gas set detector elements 810 may be configured on even rows and background set of detector elements 820 on odd rows.

The processor 612 is adapted to send control data to configure the gas set detector elements 810 to capture radiation within the high absorption wavelength band A and to configure background set detector elements 820 to capture radiation within the low absorption wavelength band B. The processor 612 is further adapted to send control data to the first infrared (IR) imaging system to trigger the capturing of a gas IR image by the gas set detector elements 810 and to trigger the capturing of a background IR image by the background set detector elements 820.

Woven Sensor Configuration—Water Image

Figure 9:
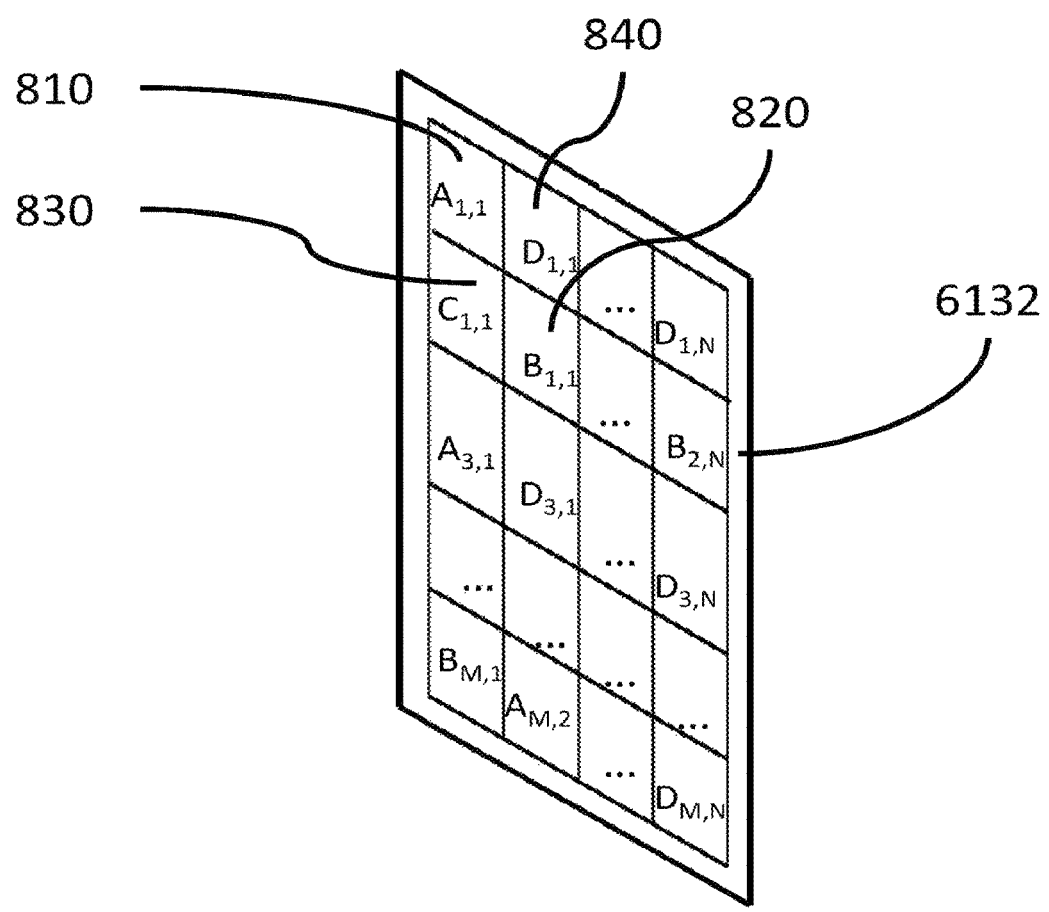
FIG. 9 shows a schematic view of a woven sensor configuration in a thermal imaging device, in accordance with one or more embodiments of the disclosure.

FIG. 9 shows a schematic view of an infrared sensor 6132 in a thermal imaging device configured to capture a gas IR image, a background IR image and a third image here called water image according to one or more embodiments addressing varying water vapor absorption or interference. This can also be referred to as a woven sensor configuration and has the additional advantages of eliminating the need for aligning or registering the gas image and the background image in addition to obtaining images used to compensate for noise/interference, e.g. due to water or steam or other gases in the scene.

A first infrared (IR) imaging system, comprised in the thermal imaging device 170 (cf. FIG. 6), comprises an image sensor 6132 configured with:
- a first set of detector elements for capturing gas related radiation, here called a gas set of detector elements $A_{row,col}$ 810;
- a second set of detector elements for capturing background related radiation, here called a background set of detector elements $B_{row,col}$ 820;
- a third set of detector elements for capturing water or water vapour related radiation, here called a water set of detector elements $C_{row,col}$ 830; and
- a fourth set of detector elements for capturing interference related radiation, here called an interference set of detector elements $D_{row,col}$ 840.

The detector elements of the plurality of different sets are configured to form blocks of detector elements. Detector elements of the gas set, the background set, the water set and the interference set are woven such that one gas detector element 810 capturing infrared radiation within a high absorption wavelength band A, one background detector element 820 capturing infrared radiation within a low absorption wavelength band B, one water detector element 830 capturing infrared radiation within a third wavelength band C and one interference detector element 840 capturing infrared radiation again within the low absorption wavelength band B is arranged in a block of four detector elements, wherein the block is repeated over part of or the entire sensor 6132.

The processor 612 is adapted to send control data to configure the gas set detector elements 810 to capture infrared radiation within the high absorption wavelength band A, to configure the background set detector elements 820 to capture infrared radiation within the low absorption wavelength band B, to configure the water set detector elements 830 to capture infrared radiation within the third wavelength band C and to configure the interference set detector elements 840 to capture infrared radiation within the low absorption wavelength band B. The processor 612 is further adapted to send control data to the first infrared (IR) imaging system to trigger the capturing of a gas IR image by the gas set detector elements 810, to trigger the capturing of a background IR image by the background set detector elements 820, to trigger the capturing of a water IR image by the water set detector elements 830 and to trigger the capturing of an interference IR image by the interference set detector elements 840.

Method Embodiments

As described above one or more embodiments relate to an improved system and method of imaging gas, in particular passive infrared imaging of gas occurring in a scene. The gas is imaged based on a difference in an estimated gas temperature $T_G$ and an estimated background temperature $T_B$. Consequently, a greater difference between $T_G$ and $T_B$ will result in a greater contrast in the imaged gas in relation to background. When the estimation of $T_G$ and $T_B$ are improved, the sensitivity of the imaging system is improved and smaller amounts of gas can be detected and optionally imaged. With improved sensitivity of the imaging system, the contrast of the imaged gas is improved, e.g. in a gas-absorption-path-length image representing the length of the path of radiation from the scene background 110 through a gas occurrence in the scene.

Embodiments described herein thus increase the sensitivity of gas detection in an image, and thereby the contrast, by an improved and dynamic selection of a high absorption wavelength band A and a low absorption wavelength band B, e.g. based on previously captured gas and background IR images.

Figure 10:
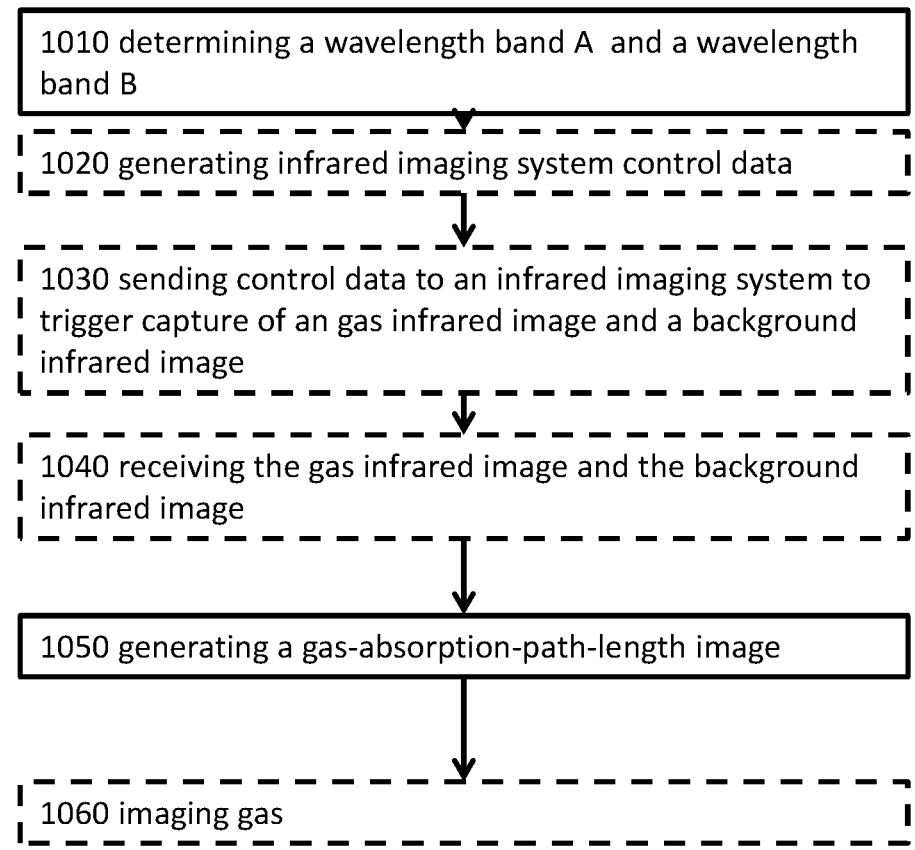
FIG. 10 is a block diagram illustrating method steps in accordance with one or more embodiments of the disclosure.

FIG. 10 shows schematically in a flow chart of a method for imaging gas in accordance with of one or more embodiments, comprising gas detection by generating a gas-absorption-path-length image. Embodiments of the method comprise a selection of the following steps:

Step 1010:

Determining, by a processor, a high absorption wavelength band A and a low absorption wavelength band B to improve contrast in a generated gas-absorption-path-length image based on a predetermined absorption spectrum of the gas, an estimated gas temperature TG and an estimated background temperature TB, wherein the high absorption wavelength band A includes an absorption wavelength band G from the absorption spectrum and wherein the low absorption wavelength band B at least partially overlaps the high absorption wavelength band A.

Further, the high absorption wavelength band A is for example determined as a subset band of a predetermined absorption spectrum including a local maximum and the low absorption wavelength band B is for example determined as a subset band of the predetermined absorption spectrum including a local minimum and partially overlapping the high absorption wavelength band A.

The step 1010 of determining the high absorption and low absorption wavelength bands may further comprise estimating the gas temperature $T_G$ and estimating the background temperature $T_B$.

An estimated gas temperature $T_B$ is for example obtained as pixel values or processed pixel values of a previously captured gas image. Estimating a gas temperature $T_B$ by processing pixel values comprised in a previously captured gas IR image may comprise a selection of:

processing pixel values of a gas IR image to a single value.

processing pixel values comprising calculating a statistical measure based on the pixel values. The statistical measure is for example a selection of an arithmetic mean, a median value, a maximum value, a minimum value or a weighted average value.

In another example the estimated gas temperature $T_G$ is obtained as a measured ambient air temperature value retrieved from an ambient air temperature sensor 619.

An estimated background temperature $T_B$ is for example obtained as pixel values or processed pixel values of a previously captured background IR image. Estimating a background temperature $T_B$ by processing pixel values comprised in a previously captured gas IR image may comprise a selection of:

processing pixel values of a background IR image to a single value.

processing pixel values comprising calculating a statistical measure based on the pixel values. The statistical measure is for example a selection of an arithmetic mean, a median value, a maximum value, a minimum value or a weighted average value.

Step 1020 Optional:

Generating infrared imaging system control data dependent on the determined high absorption wavelength band A and the low absorption wavelength band B. This step is optionally comprised in one or more embodiments.

This step comprises in one or more embodiments generating control data adapted for controlling a thermal imaging system or components thereof to capture radiation within a selection of a high absorption wavelength band A and a low absorption wavelength band B.

In one example of step 1020, infrared imaging system control data is generated as a data structure comprising data indicative of a lower endpoint of high absorption wavelength band A, a lower endpoint of a low absorption wavelength band B, a higher endpoint of high absorption wavelength band A, a higher endpoint of low absorption wavelength band B. The control data may preferably also comprise timing information for triggering the capturing of a gas IR image and a background IR image.

Step 1030 Optional:

Sending control data to trigger the capturing of an image. This step is optionally comprised in one or more embodiments.

This step typically comprises sending control data, by a processor, to an infrared imaging system to trigger the capturing of a gas IR image of a scene and to trigger the capturing of a background IR image of the scene. In examples of step 1030, the generated infrared imaging system control data is sent, from the processor 612, as a control signal to the first infrared imaging system 613 and/or the second infrared imaging system 614.

Step 1040 Optional:

Receiving, by the processor, a gas IR image and a background IR image. This step is optionally comprised in one or more embodiments.

In one example of step 1040, receiving the gas IR image and the background IR image comprises the processor 612 receiving a control signal from the first infrared imaging system 613 and/or the second infrared imaging system 614 and storing the gas IR image comprising pixel values and the background IR image comprising pixel values to a memory.

Step 1050:

Generating a gas-absorption-path-length image based on a gas IR image and a background IR image.

In one or more embodiments of step 1050, a gas-absorption-path-length image is generated for example by generating image pixel values by a selection of the following pixel operations based for example on a gas to background difference relation wherein subtraction is denoted "−" and division is denoted "/":

(gas image pixel value $A_{row,col}$–background image pixel value $B_{row,col}$);
(background image pixel value $B_{row,col}$–gas image pixel value $A_{row,col}$);
(gas image pixel value $A_{row,col}$/background image pixel value $B_{row,col}$); or
(background image pixel value $B_{row,col}$/gas image pixel value $A_{row,col}$).

The pixel values of gas IR image typically comprises a representation of the intensity of infrared radiation within the high absorption wavelength band A and the pixel values of background IR image typically comprises intensity of infrared radiation within the low absorption wavelength band B.

Step 1060 Optional:

Imaging gas and visualizing gas based on pixel values in the gas-absorption-path-length image. This step is optionally comprised in one or more embodiments.

To enable a user to understand the information in the gas-absorption-path-length image it is further imaged by generating a visual representation and presenting it on a display in the thermal imaging device or in a computing device connected to the thermal imaging device such as a tablet computer, a smartphone, a laptop or a desktop computer.

In one example of step 1060, imaging gas is performed by generating a visual representation of the gas-absorption-path-length image using false coloring, wherein generating a visual representation further comprises mapping pixel values in the gas-absorption-path-length image to a palette and generating a display gas image. In yet an example, the palette may comprise colors or greyscales from a predefined color model. The step of imaging gas would typically further comprise presenting the display gas image on a display in the thermal imaging device or on a display comprised in an external device.

Optimizing Range of A/D Converter

An aspect comprised in one or more embodiments is provided for the purpose of ensuring that the analog to digital conversion range or dynamics is used in an optimal way in the IR detector or sensor to improve contrast without limiting the gas to background temperature difference $\Delta T$ whilst remaining within the linear operating area of the detector.

A problem when imaging gas is that the sensitivity of the thermal imaging system, and thus the contrast in the gas-absorption-path-length image, is further dependent on the analog to digital conversion process. The sensors 6132, 6134 are generally generating an analog output signal, e.g. a voltage is the measurable output for bolometers. The analog signal must be analog to digital converted to obtain an image data value or pixel value. Analog to digital conversion is typically performed by an (A/D) analog to digital converter operating with an A/D working area defined as minimum A/D value, maximum A/D value and a resolution measured in number of bits. The minimum A/D value and maximum A/D value in a thermal imaging device 170, are typically limited by the operating area where the sensors 6132, 6134 have a linear response.

Figure 11:
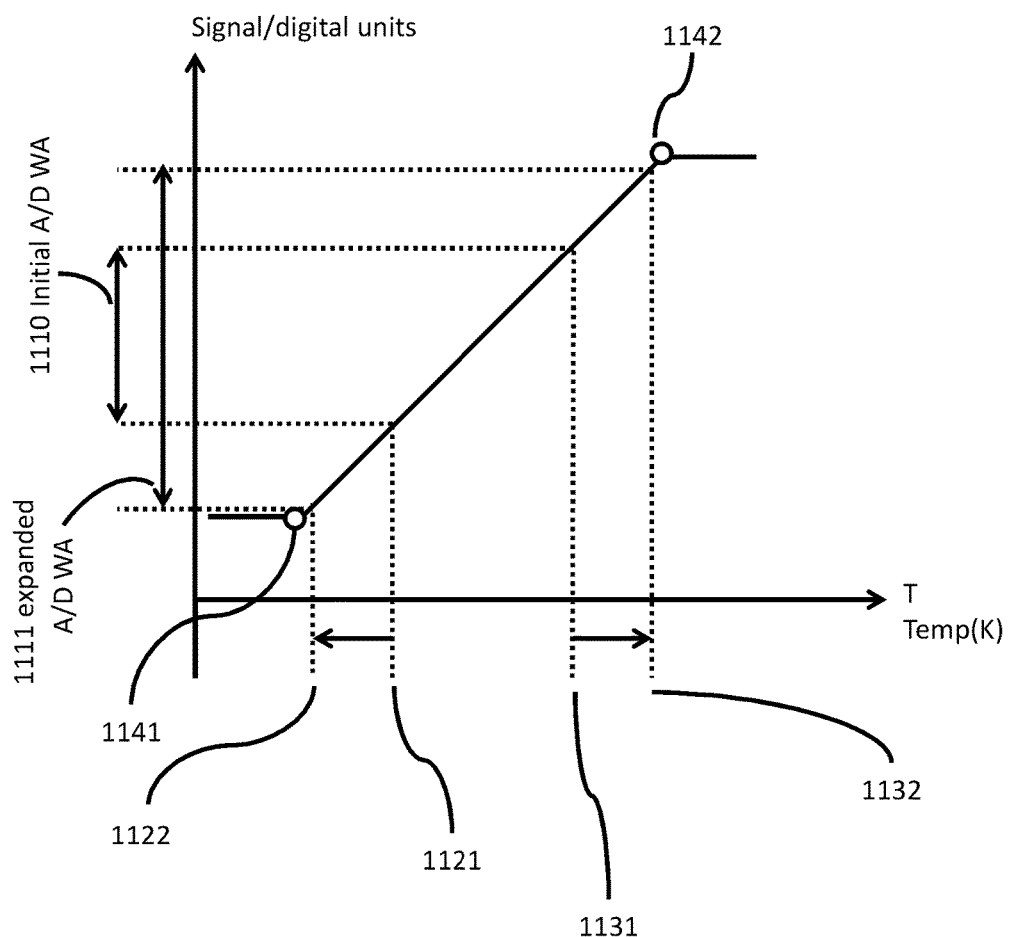
FIG. 11 shows a schematic view of an operating area of a sensor and the mapping to an A/D working area, in accordance with one or more embodiments of the disclosure.

FIG. 11 shows a schematic view of an operating area of a sensor and the mapping to A/D working area.

The sensor 6132, 6134 (cf. FIG. 6-9) has predefined response characteristics, e.g. determined by calibration measurements during the production of the thermal imaging device as a response characteristics relation. A subset of the response characteristics is linear, substantially linear or linear in practical circumstances and is limited by a minimum temperature $T_{DetMin}$ 1141 and a maximum temperature $T_{DetMin}$ 1142.

A problem is then to determine a minimum A/D value and a maximum A/D value to improve imaging of gas, i.e. improve sensitivity to detecting gas and thus contrast in the gas-absorption-path-length image. If the A/D working area, i.e. minimum A/D value and maximum A/D value, is set such that parts of the temperature range (TB–TG) or (TG–TB) is excluded the sensitivity of passive gas imaging and thus contrast in the gas-absorption-path-length image is reduced. If, on the other hand, the A/D working area, i.e. minimum A/D value and maximum A/D value, is set such that they extend below $T_{DetMin}$ 1141 and/or beyond $T_{DetMax}$ 1142, then non-linear contribution are included and the sensitivity of passive gas imaging and thus contrast in the gas-absorption-path-length image is reduced.

Typically the A/D working area can be set to a predetermined initial A/D working area, an initial minimum A/D value$_N$ 1121 and an initial maximum A/D value$_N$ 1131, selected from a predetermined set of ranges, e.g. determined by calibration measurements during the production of the thermal imaging device. According to one or more embodiments the A/D working area should be set as close to the temperature range (TB–TG) or (TG–TB) as possible. In a thermal imaging device this is controlled by changing control parameters as a detector temperature offset value $T_{offset}$ and a detector integration time $T_{int}$, wherein the detector temperature offset value $T_{offset}$ determine the initial minimum A/D value$_N$ 1121 and the detector integration time $T_{intN}$ determine the initial maximum A/D value 1131 based on a predetermined calibration relation, e.g. determined by calibration measurements during the production of the thermal imaging device.

In one example, an initial A/D working area 1110, defined by an initial minimum A/D value$_N$ 1121 as $T_{offsetN}$ and initial maximum A/D value$_N$ 1131 given by the detector integration time $T_{intN}$ and a predetermined calibration relation, is obtained, e.g. selected from a predetermined set of ranges or retrieved from memory.

Depending on if the imaged gas 160 or the background scene 110 (cf. FIG. 1) has the relatively lowest temperature an updated minimum A/D value$_{N+1}$ 1122 can be determined as background temperature TB or gas temperature TG, e.g. obtained from memory. I.e. determined as an updated minimum A/D value$_{N+1}$ 1122=minimum(TB,TG). A gas to background temperature difference $\Delta T$ 130 is calculated based on background temperature TB 122, gas temperature TG 121 and a gas to background difference relation (GSBDR) 140. An updated maximum A/D value$_{N+1}$ 1132 is determined as updated minimum A/D value$_{N+1}$ 1122+$\Delta T$ 130. Further, the updated maximum A/D value$_{N+1}$ 1132 is compared to $T_{DetMax}$ 1142 to determine that the updated maximum A/D value$_{N+1}$ 1132 is below $T_{DetMax}$ 1142. If the updated maximum A/D value$_N$ 1132 is below $T_{DetMax}$ 1142 then the updated maximum A/D value$_{N+1}$ 1132 is used as the higher limit of the A/D working area and if the maximum A/D value$_{N+1}$ 1132 is above $T_{DetMax}$ 1142 then an updated detector integration time $T_{intUpdated(N+1)}$ is determined based on the updated maximum A/D value$_{N+1}$ 1132 and an inverse predetermined calibration relation.

A new updated maximum A/D value$_{N+2}$ 1132 can be determined based on $T_{intUpdated(N+2)}$, a predetermined integration time step $\Delta T_{int}$ and the predetermined calibration relation, wherein a new updated maximum A/D value$_{N+2}$ 1132 is determined as $T_{intUpdated(N+2)}=T_{intUpdated(N+1)}-\Delta T_{int}$, wherein N is the iteration order or index.

Further, the new updated maximum A/D value$_{N+2}$ 1132 is compared to T$_{DetMax}$ 1142 to determine that the new maximum A/D value$_{N+2}$ 1132 is below T$_{DetMax}$ 1142. If so then the new updated maximum A/D value$_{N+2}$ 1132 is used as the higher limit of the A/D working area, else another iteration is performed and a new updated maximum A/D value$_{N+3}$ 1132 is determined.

Further, the updated minimum A/D value$_{N+1}$ 1122 is compared to T$_{DetMin}$ 1141 to determine that the updated minimum A/D value$_{N+1}$ 1122 is above T$_{DetMin}$ 1141. If the updated minimum A/D value$_{N+1}$ 1122 is below T$_{DetMin}$ 1141 the updated minimum A/D value$_{N+1}$ 1122 is set to T$_{DetMin}$ 1141 and is used as the lower limit of the A/D working area.

In another example, an initial A/D working area 1110, defined by an initial minimum A/D value$_N$ 1121 as T$_{offsetN}$ and initial maximum A/D value$_N$ 1131 given by T$_{intN}$ and a predetermined calibration relation, is obtained, e.g. selected from a predetermined set of ranges.

Depending on if the imaged gas 160 or the background scene 110 has the relatively lowest temperature T$_{offset}$ can be determined as TB or TG, thus as updated minimum A/D value$_N$ 1122=minimum(TB,TG). An initial T$_{intN}$ for the initial A/D working area 1010 can stepwise be increased by an integration time step $\Delta T_{1int}$ and an updated maximum A/D value$_{N+1}$ 1132 can be determined based on the initial integration time T$_{intN}$ or a integration time determined in a previous iteratation T$_{intUpdated(N)}$ integration time step $\Delta T_{int}$ and the predetermined calibration relation, wherein N is the iteration order or index, wherein T$_{intUpdated(N+1)}$ is determined as equal to (T$_{intN}$+$\Delta T_{int}$) or (T$_{intUpdated(N)}$-$\Delta T_{int}$).

Further, the updated maximum A/D value$_{N+1}$ 1132 is compared to T$_{DetMax}$ 1142 to determine that the updated maximum A/D value$_{N+1}$ 1132 is below T$_{DetMax}$ 1142. If the maximum A/D value$_{N+1}$ 1132 is above T$_{DetMax}$ 1142 then T$_{intUpdated(N+1)}$=is determined as the previously determined updated maximum A/D value$_N$ 1132 is used as the higher limit of the A/D working area else another iteration is performed and a new updated maximum A/D value$_{N+2}$ 1132 is determined.

Further, the updated minimum A/D value$_N$ 1122 is compared to T$_{Detmin}$ 1141 to determine that the updated minimum A/D value$_N$ 1122 is above T$_{DetMin}$ 1141. If the updated minimum A/D value 1122 is below T$_{DetMin}$ 1141 the updated minimum A/D value 1122 is set to T$_{DetMin}$ 1141 and is used as the lower limit of the A/D working area.

In one or more embodiments, the method comprises the steps of:

Determining an initial A/D working area 1110.
Determining an updated minimum A/D value$_{N+1}$ 1122 and an updated maximum A/D value$_{N+1}$ 1132 based on gas temperature T$_G$ and background temperature T$_B$.
Determining that the updated maximum A/D value$_{N+1}$ 1132 is below T$_{DetMax}$ 1142 and determining the updated maximum A/D value$_{N+1}$ as the higher limit of the expanded A/D working area 1111.
Determining that the updated minimum A/D value$_N$ 1122 is above T$_{DetMin}$ 1141 and determine as the lower limit of an expanded A/D working area.

A deltaT Based Optimization, Top Down

In one or more embodiments, comprising a deltaT based optimization, wherein the updated minimum A/D valueN+1 1122 is determined as minimum(T$_B$,T$_G$), the method may further comprise the following steps:

Step 1505: Obtaining a predetermined integration time step $\Delta T_{intN}$, e.g. from memory.
Step 1510: Determining a background temperature difference $\Delta T$ 130 based on T$_B$ (122), T$_G$ (121) and a gas to background difference relation (GSBDR) (140), wherein the updated maximum A/D value$_{N+1}$ (1132) is determined as updated minimum A/D value$_{N+1}$ (1122)+ $\Delta T$ (130).
Step 1515: Determining that the maximum A/D value$_{n+1}$ 1132 is above T$_{DetMax}$ 1142 and perform the following steps:
Step 1520: Determining an updated detector integration time T$_{intUpdated(N+2)}$ based on the updated maximum A/D value$_{N+1}$ 1132 and an inverse predetermined calibration relation.
Step 1525: Determining an iterated updated maximum A/D value$_{N+2}$ 1132 based on a new updated integration time T$_{intUpdated(N+2)}$, a predetermined integration time step $\Delta T_{int}$ and the predetermined calibration relation, wherein a new updated integration time is determined as T$_{intUpdated(N+2)}$=T$_{intUpdated(N+1)}$-$\Delta T_{intN}$.
Step 1530: Iterating steps 1515-1525.

Tint Based Optimization, Bottom Up

In one or more embodiments, comprising a tint bases optimization, wherein the updated minimum A/D valueN+1 1122 is determined as minimum(T$_B$,T$_G$), and wherein the initial A/D working area 1110 is defined by an initial minimum A/D value$_N$ 1121 as T$_{offsetN}$ and initial maximum A/D value$_N$ 1131 given by integration time T$_{intN}$ and a predetermined calibration relation, the method may further comprise the following steps:

Step 1605: Obtaining a predetermined integration time step $\Delta T_{int}$, e.g. from memory.
Step 1610: Determining an updated detector integration time T$_{intUpdated(N+2)}$ based on $\Delta T_{intN}$ and predetermined integration time step $\Delta T_{int}$, wherein the updated integration time is determined as T$_{intUpdated(N+1)}$=T$_{int(N)}$-$\Delta T_{int}$.
Step 1615: Determining the updated maximum A/D$_{valueN+1}$ 1132 is based on the updated detector integration time T$_{intUpdated(N+1)}$ and the predetermined calibration relation.
Step 1620: Determining that the maximum A/D value$_{n+1}$ 1132 is below T$_{DetMax}$ 1142 and perform the following steps:
Step 1625: determine an updated detector integration time T$_{intUpdated(N+2)}$ based on $\Delta T_{intN+1}$ and predetermined integration time step $\Delta T_{int}$, wherein the updated integration time is determined as T$_{intUpdated(N+2)}$=T$_{intUpdated(N+1)}$ $\Delta T_{int}$.
Step 1630: Determining updated maximum A/D value$_{N+2}$ 1132 based on the updated detector integration time T$_{intUpdated(N+2)}$ and the predetermined calibration relation.
Step 1635: Iterating steps 1620-1630

In one or more embodiments, the generated infrared imaging system control data further comprises Toffset and Tint as determined in a selection of the above method steps.

Figure 12:
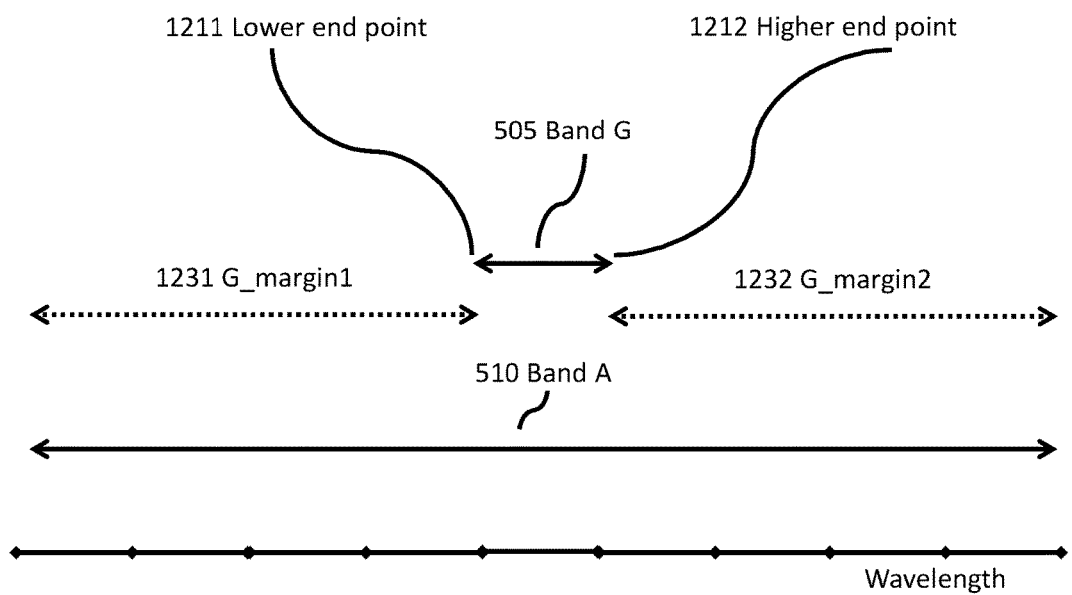
FIGS. 12, 13a, 13b, and 13c illustrate schematically how a first, high absorption wavelength band A and second, low absorption wavelength band B are determined, in accordance with one or more embodiments of the disclosure.

Determining High Absorption Wavelength Band a and Low Absorption Wavelength Band B FIG. 12 (also cf. FIGS. 2*a* and 2*b*) shows how high absorption wavelength band A 510 and low absorption wavelength band B 520 are determined in one or more embodiments. A gas related wavelength band G 505 comprising a subset of the absorption spectrum 241 of a gas in the scene and including at least a local maximum of the absorption spectrum 241 is determined. In one example wavelength band G is selected to include multiple local maxima of the absorption spectrum 241 to obtain sufficient signal to noise ratio at the sensor 613, 614 of a thermal imaging system, as would be understood by a person skilled in the art.

In one or more embodiments, determining a high absorption wavelength band A and a low absorption wavelength band B as described above further comprises: determining gas related wavelength band G based on the absorption spectrum of the gas, wherein wavelength band G is determined to include at least one local maximum of the absorption spectrum.

The wavelength band A is preferably determined to include wavelength band G 505. To safeguard that the wavelength dependent infrared radiation attenuation effect of the local maximum/maxima is captured, a lower margin G_MARGIN1 1231 and a higher margin G_MARGIN2 1232 are added to the low absorption wavelength band B 505. In one example G_MARGIN1 and G_MARGIN2 are selected in the magnitude of 5%-30% of the width of gas related wavelength band G 505. G_MARGIN1 (1231) is applied to the lower endpoint (1211) of gas related wavelength band G (505) and wavelength margin G_MARGIN2 (1232) is applied to the higher endpoint (1212) of gas related wavelength band G (505). Thus in one or more embodiments, determining a high absorption wavelength band A 510 and a low absorption wavelength band B 520 further comprises: determining the high absorption wavelength band A as including a gas related wavelength band G (505) and a predetermined wavelength margin G_MARGIN1 (1231) applied to the lower endpoint (1211) of gas related wavelength band G (505) and a predetermined wavelength margin G_MARGIN2 (1232) applied to the higher endpoint (1212) of the gas related wavelength band G (505).

Figure 13A:
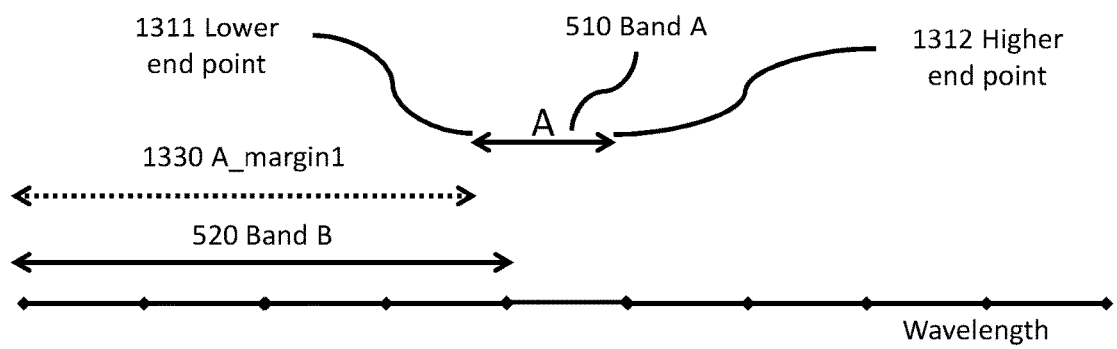

FIG. 13a shows how a high absorption wavelength band A 510 and a low absorption wavelength band B 520 are determined in one or more embodiments. The low absorption wavelength band B 520 is determined to at least partially overlap with the high absorption wavelength band A 510. To safeguard that the wavelength dependent infrared radiation attenuation effect of the local maximum/maxima is captured at the same time as eliminating the need to compensate for wavelength dependent emittance/emissivity variations, a lower margin A_MARGIN1 1331 is added to the high absorption wavelength band A 510 and applied to the lower endpoint 1311 of the high absorption wavelength band A 510. In one example, A_MARGIN1 1311 is selected in the magnitude of 50%-300% of the width of wavelength band A 510.

Figure 13B:
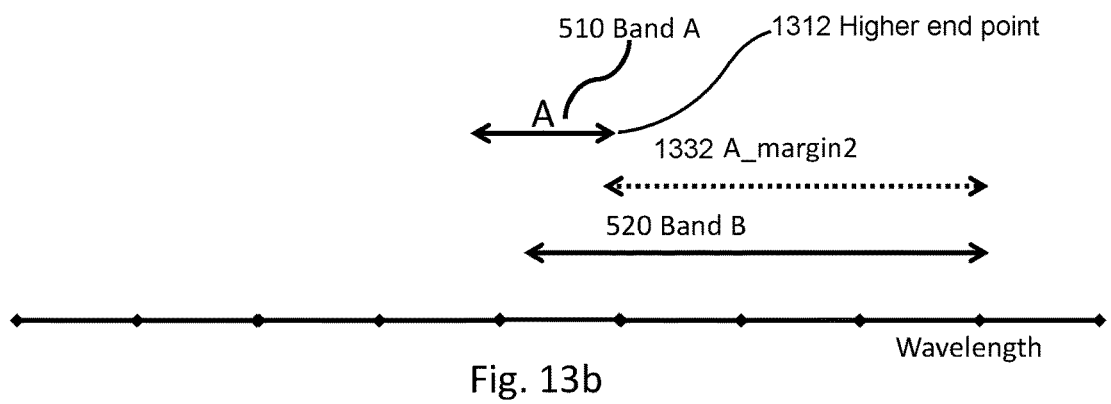

FIG. 13b shows how a high absorption wavelength band A 510 and a low absorption wavelength band B 520 are determined in one or more embodiments. The low absorption wavelength band B 520 is determined to at least partially overlap the high absorption wavelength band A 510. To safeguard that the wavelength dependent infrared radiation attenuation effect of the local maxima/s is captured at the same time as eliminating the need to compensate for wavelength dependent emittance/emissivity variations, a higher margin A_MARGIN2 1332 is added to the high absorption wavelength band A 510 and applied to the higher endpoint 1312 of the high absorption wavelength band A 510. In one example A_MARGIN2 1312 is selected in the magnitude of 50%-300% of the width of wavelength band A 510.

Figure 13C:
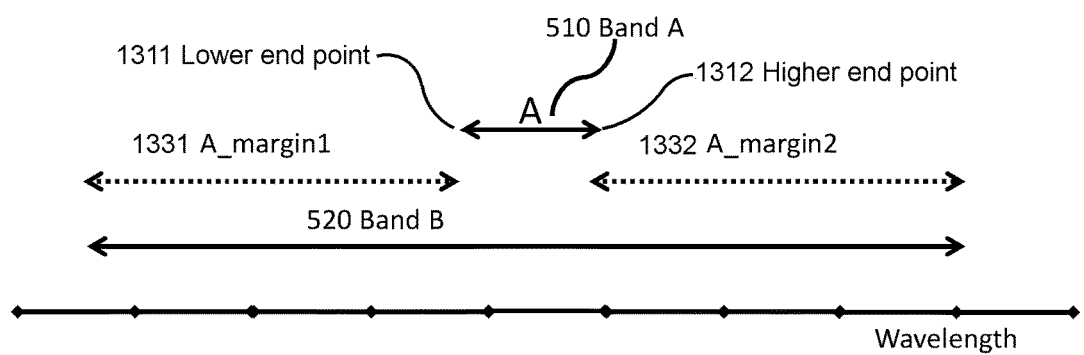

FIG. 13c shows how a high absorption wavelength band A 510 and a low absorption wavelength band B 520 are determined in one or more embodiments. The low absorption wavelength band B 520 is determined to at least partially overlap the high absorption wavelength band A 510. To safeguard that the wavelength dependent infrared radiation attenuation effect of the local maxima/s is captured at the same time as eliminating the need to compensate for wavelength dependent emittance/emissivity variations, a higher margin A_MARGIN2 1332 is added to the high absorption wavelength band A 510 and applied to the higher endpoint 1312 of the high absorption wavelength band A 510 and lower margin A_MARGIN1 1331 added to the high absorption wavelength band A 510 and applied to the lower endpoint 1311 of the high absorption wavelength band A 510. In one example A_MARGIN1 1331 and A_MARGIN2 1332 are selected in the magnitude of 50%-3000 of the width of wavelength band A 510. Thus in one or more embodiments, determining a high absorption wavelength band A 510 and a low absorption wavelength band B 520 further comprises: determining the low absorption wavelength band B 520 as having a width greater than the high absorption wavelength band A 510 and having a lower endpoint a margin A_MARGIN1 1331 below the lower endpoint 1311 of the high absorption wavelength band A 510 and/or having the higher endpoint a margin A_MARGIN2 1332 above the higher endpoint 1312 of the high absorption wavelength band A.

Dynamically Determining Wavelength Band

In one or more embodiments, a low absorption wavelength band B 520 is determined dynamically based on a preceding observation of the scene captured in a gas related image, for example a gas-absorption-path-length image generated in a preceding step.

This is, in one or more embodiments, carried out by:
generating candidate wavelength bands by shifting the low absorption wavelength band B 520 in predetermined steps relative to the high absorption wavelength band A 510;
generating a resulting absorption-path-length image based on each candidate wavelength band;
evaluating an objective function applied on the resulting gas-absorption-path-length image generated for each candidate wavelength band; and
determining the low absorption wavelength band B as the candidate wavelength band that represents a local maximum of the evaluated objective function values.

In one example a predetermined width of the low absorption wavelength band B, a wavelength band step size, an objective function and a wavelength band start position is obtained, e.g. as depicted in FIG. 13a based on A_MARGIN1 1331 or retrieved from memory. A candidate wavelength band is determined based on the wavelength band start position and a multiple of the wavelength band step size. A gas-absorption-path-length image is generated based on the candidate wavelength band, as described above, and an objective function is evaluated on the gas-absorption-path-length image to generate an objective function value, the candidate wavelength band and the corresponding objective function value is saved in memory as a pair in a data structure. The process is repeated by shifting the low absorption wavelength band B by a multiple of the wavelength band step size until a wavelength band constraint is exceeded, e.g. when the higher endpoint of the candidate wavelength band exceeds the higher endpoint of wavelength band A 510 extended by A_MARGIN2 1332 as depicted in FIG. 13b. Further, a local minimum of the objective function values is determined and an optimized wavelength band B is generated by determining the corresponding candidate wavelength band as wavelength band B 520.

A further method, in accordance with one or more embodiments, of determining a high absorption wavelength band A 510 and a low absorption wavelength band B 520 further comprises the following steps:

Step 1710:
Obtaining a predetermined width of a low absorption wavelength band B, a wavelength band step size, an objective function and a wavelength band start position.

Step 1720:
Determining a candidate wavelength by shifting the low absorption wavelength band B based on the wavelength band start position, the width of wavelength band B and a multiple of the wavelength band step size, wherein wavelength band B is shifted within a wavelength band constraint.

Step 1725:
Generating a gas-absorption-path-length image based on the candidate wavelength band.

Step 1730:
Evaluating an objective function on the pixel values comprised in the gas-absorption-path-length image to generate an objective function value.

Step 1740:
storing the candidate wavelength band and the corresponding objective function value as a pair in a data structure, e.g. to memory.

Step 1750:
Repeating method steps 1720, 1730, 1740 until a wavelength band constraint is exceeded.

Step 1760:
Determining a local maximum of the stored objective function values in each stored pair.

Step 1770:
Generating an optimized low absorption wavelength band B by determining the candidate wavelength band in the pair as low absorption wavelength band B 520.

Step 1780:
Controlling the thermal imaging system to generate a gas IR image, for example a gas-absorption-path-length image based on the optimized low absorption wavelength band B.

A further option in one or more embodiments, when determining the low absorption wavelength band B comprises excluding the absorption wavelength band G from low absorption wavelength band B.

Example of Generating a Gas-Absorption-Path-Length Image

Figure 14:
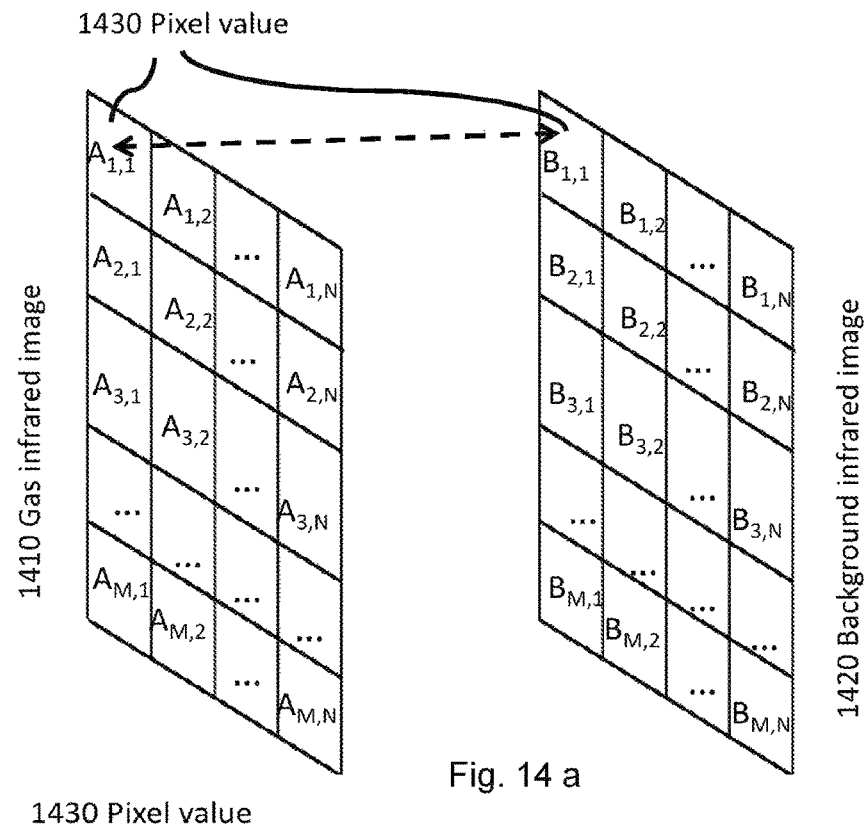
FIG. 14a illustrates schematically how a gas-absorption-path-length image is generated in a thermal imaging device comprising a first infrared imaging system, in accordance with one or more embodiments of the disclosure.
FIG. 14b illustrates schematically how a gas-absorption-path-length image is generated in a thermal imaging device comprising a first infrared imaging system and a second infrared imaging system, in accordance with one or more embodiments of the disclosure.
Figure 14:
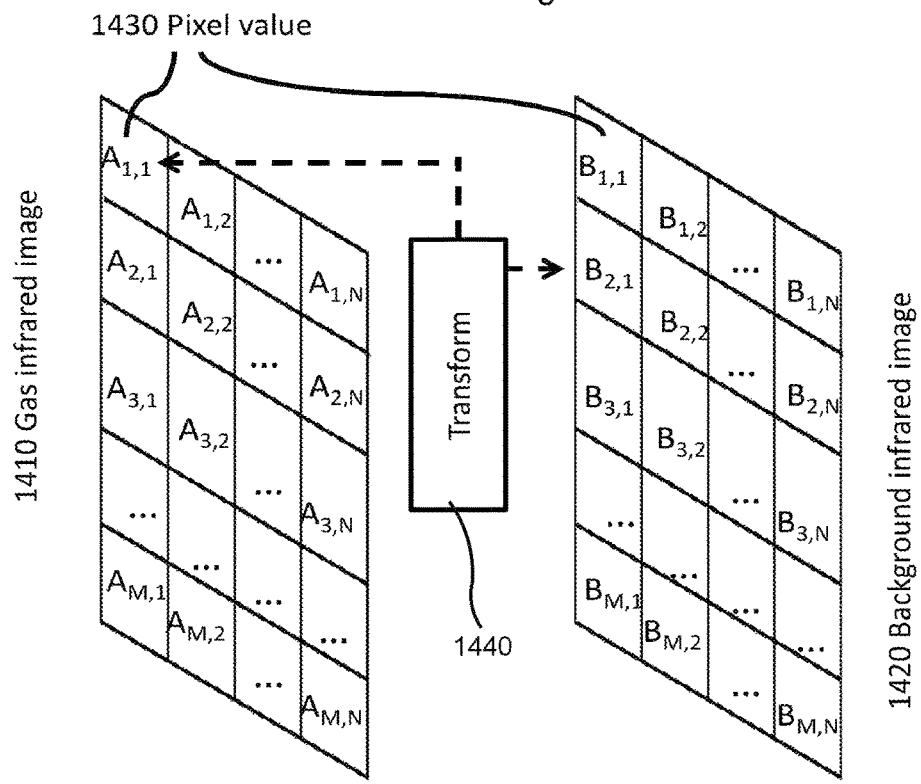

FIG. 14*a* illustrates schematically how a gas-absorption-path-length image is generated in accordance with one or more embodiments, with a thermal imaging device 170 comprising an infrared thermal imaging system 613, e.g. as depicted e.g. in FIGS. 6 and 7*b* to 9. In this example, the same thermal imaging system is used to capture a gas IR image as well as a background IR image. FIG. 14*a* illustrates a gas IR image 1410 and a background IR image 1420 with their respective pixel values 1430, $A_{M,N}$ and $B_{M,N}$ respectively. The optical axis and the field of view (FOV) are then identical, thus pixel values comprised in the gas image and pixel values comprised in the background image always represent the same part of the scene 110 before combining them to a pixel value comprised in the gas-absorption-path-length image.

A gas-absorption-path-length image is, in accordance with one or more embodiments of this kind, thus generated by pixel operations using pixel values from the gas IR image and the background IR image. Different examples comprises a selection of the following operations:

gas-absorption-path-length image pixel value$_{1,1}$=$A_{1,1}$−$B_{1,1}$;

gas-absorption-path-length image pixel value$_{1,1}$=$B_{1,1}$−$A_{1,1}$;

gas-absorption-path-length image pixel value$_{1,1}$=$B_{1,1}$/$A_{1,1}$; and/or gas-absorption-path-length image pixel value$_{1,1}$=$A_{1,1}$/$B_{1,1}$.

FIG. 14*b* illustrates schematically how a gas-absorption-path-length image is generated in accordance with one or more embodiments, with a thermal imaging device 170 comprising a first infrared imaging system 613 and a second infrared imaging system 614, e.g. as depicted in FIGS. 6 and 7*a*. In this example, different thermal imaging systems are used to capture a gas IR image and a background IR image. FIG. 14*b* illustrates a gas IR image 1410 and a background IR image 1420 with their respective pixel values 1430, $A_{M,N}$ and $B_{M,N}$ respectively. The optical axis and the field of view (FOV) may differ leading to different parallax errors and/or different FOV size. To ensure that pixel values comprised in the gas image and pixel values comprised in the background image represent the same part of the scene 110 before combining them to a pixel value comprised in the gas-absorption-path-length image, they are registered or transformed into one coordinate system through a transform 1440, e.g. intensity-based registration, feature-based registration by using linear or elastic transformations.

A gas-absorption-path-length image is, in accordance with one or more embodiments of this kind, thus generated by pixel operations using pixel values from the gas IR image and the background IR image. Different examples comprises a selection of the following operations:

gas-absorption-path-length image pixel value$_{1,1}$=$A_{1,1}$−$B_{2,1}$;

gas-absorption-path-length image pixel value$_{1,1}$=$B_{2,1}$−$A_{1,1}$;

gas-absorption-path-length image pixel value$_{1,1}$=$B_{2,1}$/$A_{1,1}$; and/or gas-absorption-path-length image pixel value$_{1,1}$=$A_{1,1}$/$B_{2,1}$.

Figure 15:
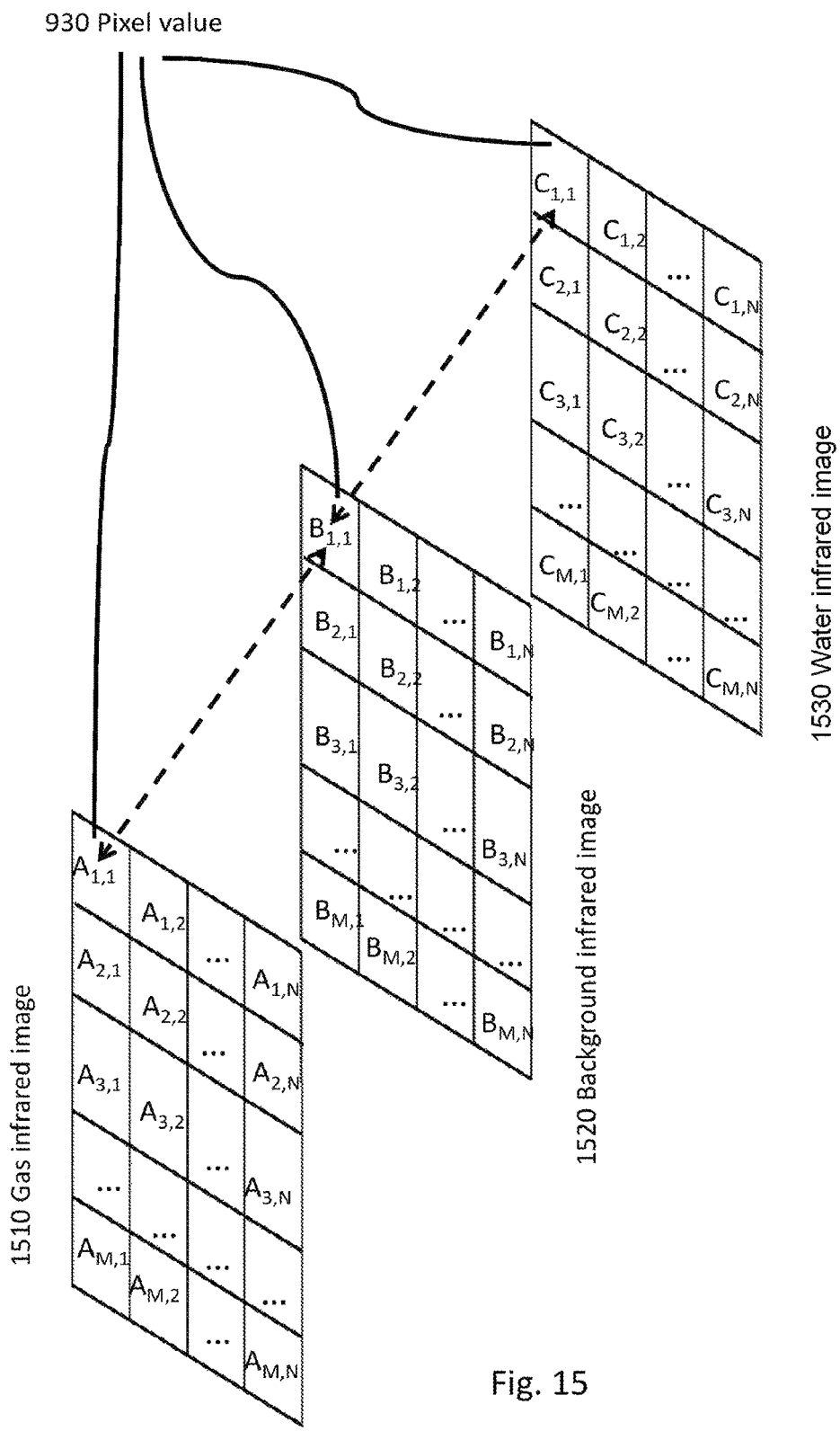
FIG. 15 illustrates schematically how a gas-absorption-path-length image is generated in a thermal imaging device by compensating for water attenuation of infrared radiation, in accordance with one or more embodiments of the disclosure.

FIG. 15 illustrates schematically how a gas-absorption-path-length image is generated in accordance with one or more embodiments, by compensating for water attenuation of infrared radiation using a thermal imaging device with one or more infrared imaging systems as described above. The sensitivity to detecting gas and thus contrast in the gas-absorption-path-length image is further improved by generating the gas-absorption-path-length image further based on a water IR image. A third, water related, wavelength band C is determined to improve contrast in a generated gas-absorption-path-length image based on a predetermined water absorption spectrum. The water related wavelength band C includes at least a local minimum of the water absorption spectrum and preferably excludes both the high absorption wavelength band A and the low absorption wavelength band B. By determining the attenuation of infrared radiation in a wavelength band where the absorption spectrum for water has a at least a local minimum and where the gas show no or very low attenuation of infrared radiation, a measure of water attenuation in the water related wavelength band C, can be approximated to be valid also for the high absorption wavelength band A and the low absorption wavelength band B, thus the contribution of water attenuation can be compensated for. In one or more embodiments, water related wavelength band C is indicated in data comprised in infrared imaging system control data sent to the infrared imaging system. A water IR image is captured by the high absorption or second infrared imaging system 613, 614 triggered by the control data, wherein the water IR image comprises intensity of infrared radiation within water related wavelength band C. The processor 612 receives the water IR image and generates an improved gas-absorption-path-length image based on a gas image, a background image and the water image;

A gas-absorption-path-length image is, in accordance with one or more embodiments of this kind, thus generated by pixel operations using pixel values from the gas IR image, the water IR image and the background IR image. Different examples of generating a gas-absorption-path-length image by combining pixel values comprised in the gas image, pixel values comprised in the background image and pixel values comprised in the water image comprises a selection of the following operations:

a gas-absorption-path-length image pixel $value_{1,1} = A_{1,1} - B_{1,1+} - C_{1,1}$; and/or gas-absorption-path-length image pixel $value_{1,1} = B_{1,1} - A_{1,1} +- C_{1,1}$.

Aligning

Since the gas and background IR image may be captured at different instances in time the thermal imaging device might be moved in a way such that the offset, direction and rotation around the optical axis differ between a gas IR image and a background IR image. Similarly, in one or more embodiments with multiple infrared imaging systems 613, 614, the orientation of optical axis of the first infrared imaging system 613 and the second infrared imaging system 614 might differ. This results in an optical phenomenon known as parallax distance error, parallax pointing error and parallax rotation error. Due to these parallax errors, the captured view of the real world scene might differ between IR images. In order to combine the gas image and the background image, the images must be adapted so that an adapted gas IR image and an adapted background IR image, representing the same part of the scene, is obtained, in other words, compensating for the different parallax errors and FOV size. This processing step is referred to as image registration or alignment of the first image and the second image, i.e. the process of transforming different sets of data into one coordinate system through a transform. Registration or alignment can be performed according to any method known to a skilled person in the art, e.g. intensity-based, feature-based registration using linear or elastic transformations.

Displaying Visualizing an Image, IR Image or Gas Image

As thermal images by nature are generally low contrast and noisy, the captured IR image or gas-absorption-path-length image may be subjected to various imaging processing in order to improve the interpretability of the image before displaying it to a user. Examples of such image processing is correction with IR temperature calibration data parameters, low pass filtering, registration of multiple successive IR image or gas images and averaging to obtain an averaged IR image or gas image or any other IR image or gas image processing operation known to a person skilled in the art. As infrared radiation is not visible to the human eye there are no natural relations between the captured IR image's or gas image's data values of each pixel in an IR image or gas image and the greyscale or the colors displayed on a display. Therefore, an information visualization process referred to as false coloring or pseudo coloring is used to map image data values or pixel values of each pixel in an IR image or gas-absorption-path-length to a palette used to present the corresponding pixel displayed on a display, e.g. using greyscale or colors.

A palette is typically a finite set of color or grey-scale representations selected from a color model for the display of images or visual representations of IR images/gas-absorption-path-length images, i.e. a pre-defined palette represents a finite set of grayscale or color values of a color model displayable on a display thereby making it visible to the human eye. Mapping of captured infrared (IR) image data values of each pixel in an IR image or gas image data values of each pixel in a gas image to a palette used to present the corresponding pixel of a visual representation of said IR image displayed on a display is typically performed by applying a pre-determined relation. Such a pre-determined relation typically describes a mapping from image data values or pixel values to said pre-defined palette, e.g. a palette index value with an associated color or grey-scale representation selected from a color model. The gas visualizing IR image or gas-absorption-path-length image is typically displayed to an intended user based on the gas-absorption-path-length image data values or pixel values of each pixel in a gas-absorption-path-length image, optionally IR temperature calibration data parameters, a predefined palette representing a finite set of grayscale or color values of a color model displayable on a display and a pre-determined relation describing a mapping from infrared image data values or gas-absorption-path-length image pixel values to said pre-defined palette.

The processor of described thermal imaging devices is, in accordance with one or more embodiments, configured to perform a selection of any or all of the method steps described herein that are associated with processing of captured IR images or gas-absorption-path-length images comprising image data values or pixel values, such as selection of data values/pixel values, mapping of temperature values associated with the data values/pixel values to color and/or grayscale values, assigning each pixel of a frame of IR data values a representation value from a preselected color model, e.g. based on the associated temperature value of said pixel, and other operations described herein.

In one or more embodiments, there is provided a computer-readable medium on which is stored:

non-transitory information for performing a method according to any of the embodiments described herein; and/or non-transitory information configured to control a processor/processing unit to perform any of the steps or functions of embodiments described herein.

In one or more embodiments, there is provided a computer program product comprising code portions adapted to control a processor to perform any of the steps or functions of any of the embodiments described herein. Software in accordance with the present disclosure, such as program code portions and/or data, can be stored in non-transitory form on one or more machine-readable mediums. It is also contemplated that software identified herein can be implemented using one or more general purpose or specific purpose computers and/or computer systems, networked and/or otherwise.

Where applicable, one or more embodiments provided by the present disclosure can be implemented using hardware, software, or combinations of hardware and software. Also where applicable, the various hardware components and/or software components set forth herein can be combined into composite components comprising software, hardware, and/or both. Where applicable, the various hardware components and/or software components set forth herein can be separated into sub-components comprising software, hardware, or both. In addition, where applicable, it is contemplated that software components can be implemented as hardware components, and vice-versa. Where applicable, the ordering of various steps described herein can be changed, combined into composite steps, and/or separated into sub-steps to provide features described herein.

The foregoing disclosure is not intended to limit the present invention to the precise forms or particular fields of use disclosed. It is contemplated that various alternate embodiments and/or modifications to the present invention, whether explicitly described or implied herein, are possible in light of the disclosure. Accordingly, the scope of the invention is defined only by the claims.

The invention claimed is:

1. A method comprising:
    determining a temperature of a background of a scene and a temperature of a gas in the scene disposed between the background and a thermal imaging system;
    identifying a subset of a predetermined absorption spectrum of the gas based on the determined temperatures of the gas and the background;
    controlling the thermal imaging system to capture:
        a gas infrared (IR) image in response to radiation received in a high absorption wavelength band A for the gas in the predefined absorption spectrum and comprising the subset of the predetermined absorption spectrum, and
        a background IR image in response to radiation received in a low absorption wavelength band B for the gas in the predefined absorption spectrum; and
    generating a gas-absorption-path-length image, which represents the length of the path of radiation from the background through the gas, based on the gas IR image and the background IR image.

2. The method of claim 1, further comprising:
    generating a gas visualization image based on the gas-absorption-path-length image.

3. The method of claim 2, wherein:
    the gas visualization image is generated based on pixel values of the gas-absorption-path-length image and a palette; and
    the palette comprises grayscales and/or colors associated with mutually exclusive ranges of pixel values.

4. The method of claim 1, wherein:
    the high absorption wavelength band A is determined to include an absorption wavelength band G determined to include at least a local maximum of the absorption spectrum;
    the low absorption wavelength band B is determined to at least partially overlap the high absorption wavelength band A; and/or
    the low absorption wavelength band B is determined to exclude the absorption wavelength band G.

5. The method of claim 4, wherein:
    the absorption wavelength band G comprises at least a local maximum of the absorption spectrum; and
    the high absorption wavelength band A comprises the absorption wavelength band G with or without a predetermined wavelength margin.

6. The method of claim 5, wherein the predetermined wavelength margin is a selection of:
    a first wavelength margin G_MARGIN1 applied to the lower endpoint of the absorption wavelength band G; and/or
    a second wavelength margin G_MARGIN2 applied to the higher endpoint of the absorption wavelength band G.

7. The method of claim 1, wherein the low absorption wavelength band B has a width greater than the high absorption wavelength band A with or without a predetermined wavelength margin.

8. The method of claim 7, wherein the predetermined wavelength margin is a selection of:
    a first wavelength margin A_MARGIN1 below the lower endpoint of the high absorption wavelength band A; and/or
    a second wavelength margin A_MARGIN2 above the higher endpoint of the high absorption wavelength band A.

9. The method of claim 1, further comprising determining the low absorption wavelength band B, wherein the determining the low absorption wavelength band B comprises:
    generating candidate wavelength bands for the low absorption wavelength band B by varying the width of and/or shifting, within a band constraint, a predetermined wavelength band relative to the high absorption wavelength band A;
    generating corresponding gas-absorption-path-length images based on the candidate wavelength bands;
    evaluating the gas-absorption-path-length images generated based on the corresponding candidate wavelength bands using an objective function that is indicative of an amount of contrast in each gas-absorption-path-length image; and
    choosing one of the candidate wavelength bands that results in the highest contrast absorption-path-length image according to the objective function as the determined low absorption wavelength band B.

10. The method of claim 1, further comprising:
    determining a water wavelength band C based on a predetermined water absorption spectrum to improve contrast in the generated gas-absorption-path-length image, wherein the water wavelength band C excludes the high absorption wavelength band A and/or the low absorption wavelength band B;
    controlling the thermal imaging system to capture a water image in response to radiation received within the water wavelength band C; and
    wherein the gas-absorption-path-length image exhibits an increased gas contrast further based on the water image.

11. The method of claim 1, wherein:
    the determined background temperature $T_B$ is based on a previously captured background IR image; and/or
    the determined gas temperature $T_G$ is based on a measured ambient air temperature retrieved from an ambient air temperature sensor and/or based on a previously captured gas IR image.

12. The method of claim 1, wherein the generating the gas-absorption-path-length image is further based on a gas to background difference relation that describes a relationship between gas IR image pixel values and background IR image pixel values.

13. A thermal imaging device comprising:
    an infrared (IR) imaging system controllable to capture a gas infrared (IR) image representing the temperature of a gas and a background IR image representing the temperature of a background;
    a memory; and
    a processor communicatively coupled to the IR imaging system and the memory, the processor being configured to:
        determine a temperature of a background of a scene and a temperature of a gas in the scene disposed between the background and the IR imaging system;

identify a subset of a predetermined absorption spectrum of the gas based on the determined temperatures of the gas and the background;
control the IR imaging system to capture:
the gas IR image in response to radiation received in a high absorption wavelength band A for the gas in the predefined absorption spectrum and comprising the subset of the predetermined absorption spectrum, and
the background IR image in response to radiation received in a low absorption wavelength band B for the gas in the predefined absorption spectrum; and
generate a gas-absorption-path-length image, which represents the length of the path of radiation from the background through the gas, based on the gas IR image and the background IR image.

14. The thermal imaging device of claim 13, wherein the IR imaging system comprises:
a first IR imaging system comprising a first uncooled IR sensor and a first optical filter, the first IR imaging system being configured or controllable to capture the radiation in the high absorption wavelength band A; and
a second IR imaging system comprising a second uncooled IR sensor and a second optical filter, the second IR imaging system being configured or controllable to capture the radiation in the low absorption wavelength band B.

15. The thermal imaging device of claim 13, wherein:
the high absorption wavelength band A is determined to include an absorption wavelength band G with or without a predetermined wavelength margin;
the absorption wavelength band G is determined to include at least a local maximum of the absorption spectrum;
the low absorption wavelength band B is determined to at least partially overlap the high absorption wavelength band A; and/or
the low absorption wavelength band B is determined to exclude the absorption wavelength band G.

16. The thermal imaging device of claim 13, wherein the IR imaging system comprises an analog-to-digital (A/D) converter configured to have an operating range with a minimum A/D value extending below an A/D value corresponding to an expected minimum temperature of the gas and the background and with a maximum A/D value extending above an A/D value corresponding to an expected maximum temperature of the gas and the background.

17. The thermal imaging device of claim 13, wherein the processor is configured to:
determine the background temperature TB based on a previously captured background IR image retrieved from the memory; and/or
determine the gas temperature $T_G$ based on a measured ambient air temperature retrieved from an ambient air temperature sensor of the thermal imaging device and/or based on a previously captured gas IR image retrieved from the memory.

18. The thermal imaging device of claim 13, wherein the processor is configured to:
determine a water wavelength band C based on a predetermined water absorption spectrum to improve contrast in the generated gas-absorption-path-length image, wherein the water wavelength band C excludes the high absorption wavelength band A and/or the low absorption wavelength band B;
control the thermal imaging system to capture a water image in response to radiation received within the water wavelength band C; and
wherein the gas-absorption-path-length image exhibits an increased gas contrast further based on the water image.

19. A non-transitory computer-readable medium storing instructions which, when executed by a processor of a thermal imaging device, cause the thermal imaging device to perform a method comprising:
determining a temperature of a background of a scene and a temperature of a gas in the scene disposed between the background and the thermal imaging device;
identifying a subset of a predetermined absorption spectrum of the gas based on the determined temperatures of the gas and the background;
controlling the thermal imaging device to capture:
a gas infrared (IR) image in response to radiation received in a high absorption wavelength band A for the gas in the predefined absorption spectrum and comprising the subset of the predetermined absorption spectrum, and
a background IR image in response to radiation received in a low absorption wavelength band B for the gas in the predefined absorption spectrum; and
generating a gas-absorption-path-length image, which represents the length of the path of radiation from the background through the gas, based on the gas IR image and the background IR image.

* * * * *

UNITED STATES PATENT AND TRADEMARK OFFICE
CERTIFICATE OF CORRECTION

PATENT NO. : 10,422,741 B2  Page 1 of 1
APPLICATION NO. : 15/692805
DATED : September 24, 2019
INVENTOR(S) : Jonas Sandsten and Erik Ekerot It is certified that error appears in the above-identified patent and that said Letters Patent is hereby corrected as shown below:

In the Specification

In the Detailed Description:

In Column 17, Line 24, change "$\Delta T_{Int}$" to --$\Delta T_{int}$--.

In Column 17, Line 30, change "$(T_{intUpdated(N)} - \Delta T_{int})$" to --$(T_{intUpdated(N)} + \Delta T_{int})$--.

In Column 18, Line 32, change "$T_{intUpdated(N+2)}$" to --$T_{intUpdated(N+1)}$--.

In Column 18, Lines 34-35, change "$T_{intUpdated(N+1)} = T_{int(N)} - \Delta T_{int}$" to --$T_{intUpdated(N+1)} = T_{int(N)} + \Delta T_{int}$--.

In Column 18, Lines 47-48, change "$T_{intUpdated(N+2)} = T_{intUpdated(N+1)} \Delta T_{int}$" to --$T_{intUpdated(N+2)} = T_{intUpdated(N+1)} + \Delta T_{int}$--.

In Column 20, Line 12, change "50%-3000" to --50%-300%--.

Signed and Sealed this
Tenth Day of December, 2019

Andrei Iancu
*Director of the United States Patent and Trademark Office*